(12) United States Patent
Takano

(10) Patent No.: US 10,100,949 B2
(45) Date of Patent: Oct. 16, 2018

(54) CHECK-VALVE AND MICROCHEMICAL CHIP USING THE SAME

(71) Applicant: ASAHI FR R&D CO., LTD., Saitama-shi, Saitama (JP)

(72) Inventor: Tsutomu Takano, Saitama (JP)

(73) Assignee: ASAHI FR R&D CO., LTD., Saitama (JP)

( * ) Notice: Subject to any disclaimer, the term of this patent is extended or adjusted under 35 U.S.C. 154(b) by 0 days.

(21) Appl. No.: 15/568,143

(22) PCT Filed: Apr. 27, 2016

(86) PCT No.: PCT/JP2016/063192
§ 371 (c)(1),
(2) Date: Oct. 20, 2017

(87) PCT Pub. No.: WO2016/178395
PCT Pub. Date: Nov. 10, 2016

(65) Prior Publication Data
US 2018/0066769 A1    Mar. 8, 2018

(30) Foreign Application Priority Data

May 1, 2015 (JP) .................................. 2015-094148

(51) Int. Cl.
| | |
|---|---|
| *F16K 15/14* | (2006.01) |
| *F16K 99/00* | (2006.01) |
| *B01J 19/00* | (2006.01) |
| *B81B 3/00* | (2006.01) |
| *C12M 1/00* | (2006.01) |
| *G01N 37/00* | (2006.01) |
| *B01L 3/00* | (2006.01) |
| *G01N 27/447* | (2006.01) |

(52) U.S. Cl.
CPC .......... *F16K 99/0057* (2013.01); *B01J 19/00* (2013.01); *B01L 3/502738* (2013.01);
(Continued)

(58) Field of Classification Search
CPC ................. F16K 99/0057; F16K 15/14; B01L 3/502738; B01L 2400/0605; G01N 27/44791
See application file for complete search history.

(56) References Cited

U.S. PATENT DOCUMENTS

| | | | |
|---|---|---|---|
| 4,895,500 A * | 1/1990 | Hok ...................... | F04B 43/043 137/512.4 |
| 6,431,212 B1 | 8/2002 | Hayenga et al. | |

(Continued)

FOREIGN PATENT DOCUMENTS

| | | |
|---|---|---|
| JP | 2003-534504 A | 11/2003 |
| JP | 2005-016610 A | 1/2005 |

(Continued)

OTHER PUBLICATIONS

Jul. 19, 2016 Written Opinion of the International Searching Authority issued in Patent Application No. PCT/JP2016/063192.
(Continued)

*Primary Examiner* — P. Macade Nichols
(74) *Attorney, Agent, or Firm* — Oliff PLC

(57) ABSTRACT

A check-valve comprises: a thin sheet and a thick sheet; flow paths for flowing fluid which are formed by penetrating the thin sheet and the thick sheet; a flow-in chamber and a flow-out chamber which are connected to the flow paths; a partition sheet which is bonded to the thin sheet and the thick sheet while being sandwiched therebetween, and has a flexible inner flange which projects in cavities of the flow-in chamber and the flow-out chamber and does not close the flow-out valve chamber by flexing toward the flow-out valve chamber in a normal flow, and closes the flow-in valve chamber by flexing toward the flow-in valve chamber in a reverse flow; and a through-pass hole which is opened at the partition sheet and connects the both valve chambers.

10 Claims, 12 Drawing Sheets

(52) U.S. Cl.
CPC .............. *B81B 3/00* (2013.01); *B81B 3/0054* (2013.01); *C12M 1/00* (2013.01); *F16K 15/14* (2013.01); *G01N 27/44791* (2013.01); *G01N 37/00* (2013.01); *G01N 37/005* (2013.01); *B01L 2400/0605* (2013.01); *H05K 999/99* (2013.01)

(56) References Cited

U.S. PATENT DOCUMENTS

| | | | | |
|---|---|---|---|---|
| 8,528,591 | B2* | 9/2013 | Pirk | F04B 43/043 137/493.8 |
| 2002/0155010 | A1* | 10/2002 | Karp | B01L 3/502738 417/413.2 |
| 2006/0042698 | A1 | 3/2006 | Koeneman et al. | |

FOREIGN PATENT DOCUMENTS

| | | |
|---|---|---|
| JP | 2005-283331 A | 10/2005 |
| JP | 2005-337415 A | 12/2005 |
| JP | 2008-517218 A | 5/2008 |

OTHER PUBLICATIONS

Jul. 19, 2016 International Search Report issued in Patent Application No. PCT/JP2016/063192.

Oct. 13, 2015 Office Action issued in Japanese Patent Application No. 2015-094148.

* cited by examiner

CHECK-VALVE AND MICROCHEMICAL CHIP USING THE SAME

TECHNICAL FIELD

The present invention relates to a check-valve used in an apparatus for conducting microanalysis of a biological component, which is included in a test sample of a specimen originated from a biological object, and a microchemical chip for chemical microsynthesis of a useful substance such as the biological component etc. exhibiting a pharmacological action.

BACKGROUND OF THE ART

In order to quantitate a reaction amount of an enzyme which acts on a substrate in a specimen or an amount of the substrate by degree of color generation depending on a reagent which is colored by the enzyme or substrate, a microbiological chip has been used. In this regard, specific substrate selectivity of the enzyme is utilized by using a trace amount like μL order of a test sample such as blood, urine and the like, which are the specimen originated from a biological object. Further, when a quantitative analysis of a substrate amount by converting an enzyme reaction amount into an electric signal by using a membrane including the enzyme and electrodes, DNA extraction and PCR amplification (polymerase chain reaction amplification) thereof, ion concentration measurement, microsynthesis of nucleic acid, saccharide, protein or peptide and the like are conducted in μM order, a microreactor chip has been used.

A microchemical chip such as the microbiological chip and microreactor chip has a channel-shaped micro flow path having tens to hundreds μm in width as a reaction channel which mixes, reacts, divides and detects the liquid specimen and a reagent which are pumped and flowed by pressurizing. When the liquid specimen and the reagent are mixed and reacted, the liquid specimen which flows in the micro flow path is flowed only in one direction, stopped and held in a reaction cistern. Such the flow of the liquid specimen has to be controlled.

A micro valve used in control of the above flow is disclosed in Patent Document 1. The micro valve disclosed therein comprises a valve chamber formed into a half way of a line of a flow path which flows a liquid such as a liquid specimen; a valve made from silicone rubber which partitions the valve chamber into two chambers; and a pressure chamber formed on a location corresponding to be located immediately above the valve chamber. According to the micro valve, the valve is closed by pressurization of the valve chamber through flow-in of pressurized air or is opened by depressurization of the valve chamber through vacuuming up air and thus, the flow path is opened and occluded. In the micro valve, since the volume of the two chambers is mutually different by the biased location of the valve in the valve chamber, difference in pressure of the fluid which is held therein may be utilized. Thereby a function of a check-valve may be given to the micro valve.

According to the micro valve of Patent Document 1, in order to open and close the valve, a motive power source such as a pump or a piezoelectric material, which directly pressurizes or depressurizes the valve chamber from above, is essential. Further when the function of the check-valve is given to the micro valve, the valve chamber having a large volume is required. A structure of the micro valve therefore has been complexed. Furthermore because design of a microchemical chip is restricted by a large amount of the valve chamber, miniaturization thereof has been difficult. In addition, the liquid specimen and the reagent are held in the valve chamber having the large volume, and are not smoothly flowed. Quick analysis and measurement thereof have been difficult.

PRIOR ART DOCUMENT

Patent Document

[Patent Document 1] Japanese Patent Application Publication No. 2005-337415A

SUMMARY OF THE INVENTION

Problems to be Solved by the Invention

The present invention was made in view of solving the above described problems, and its object is to provide a check-valve not requiring any motive power sources such as a pump and a piezoelectric element for directly pressurizing and depressurizing for a valve chamber from the above, which is capable of making its size compact by a simple structure and further capable of stopping positively a reverse flow while flowing smoothly a specimen and a reagent, and a microchemical chip using the same.

Means for Solving Problems

A check-valve of the present invention developed to achieve the objects described above comprises plural valve chamber forming members; a flow-in valve chamber and a flow-out valve chamber which are constituted by overlapping in the plural valve chamber forming members and connected to each of flow paths in which fluid flows; a partition sheet which is bonded to the plural valve chamber forming members while being sandwiched therebetween and has a flexible inner flange in cavities of the flow-in valve chamber and the flow-out valve chamber, in which the flexible inner flange does not close the flow-out valve chamber by flexing toward the flow-out valve chamber in a normal flow, and closes the flow-in valve chamber by flexing toward the flow-in valve chamber in a reverse flow; and a through-pass part which penetrates the inner flange.

In the check-valve, the flow-in valve chamber is preferably shallower than the flow-out valve chamber.

In the check-valve, the flow path penetrates at least one of the plural valve chamber forming members, and a base sheet and a covering sheet are bonded to an outermost part of the plural valve chamber forming members, respectively.

In the check-valve, the through-pass part may be a through-pass hole which is opened at the inner flange or a slit which is cut in the inner flange.

In the check-valve, the fluid is preferably liquid, and a contact angle between the liquid and an inner face of the flow-in valve chamber and a contact angle between the liquid and an inner face of the flow-out valve chamber may be mutually different.

In the check-valve, the partition sheet is preferably made from an elastomer having hardness from 20 to 70 in Shore-A hardness.

In the check-valve, the elastomer may be silicone rubber, butyl rubber, ethylene-propylene rubber, ethylene-propylene-diene rubber, urethane rubber, fluoro rubber, acryl rubber, butadiene rubber, styrene-butadiene rubber, acrylonitrile-butadiene rubber, chloroprene rubber, isoprene rubber, natural rubber and/or a thermoplastic elastomer.

In the check-valve, the partition sheet may have a thickness from 20.0 to 200 μm.

In the check-valve, a magnetic material is preferably embedded and/or attached, and the inner flange is flexed corresponding to magnetic force from external side.

A microchemical chip of the present invention comprises at least one of the above check-valve; and an inlet/outlet which is connected to external side at one end of the respective flow paths.

In the microchemical chip, one of the inlet/outlet may be a liquid specimen inlet, and the other of the inlet/outlet may be a liquid specimen outlet or a gas outlet.

Effects of the Invention

The check-valve of the present invention has a simple structure, i.e. the plural valve chamber forming members and the partition sheet are stacked and bonded. Since a motive power source which directly pressurizes and depressurizes an inner flange from the above is not required, the check-valve can be compact. Further the check-valve can be quickly produced with a low cost.

The check-valve does not occlude a flow-out valve chamber by a normal flow of fluid, and occludes a flow-in valve chamber by a reverse flow of the fluid. Since the reverse flow thereof can be stopped by slight motion of the inner flange, a volume of the valve chamber can be small. According to the check-valve, the fluid of the normal flow can be smoothly flowed, and the fluid of the reverse flow can be reliably stopped.

According to the microchemical chip having the above check-valve of the present invention, because the flow which is flowing, stopping and holding the fluid in a flow path can be controlled at will, a liquid specimen and a reagent can be arbitrarily mixed, reacted and divided, or a desirable component can be detected.

MODE FOR CARRYING OUT THE INVENTION

Figure 1:
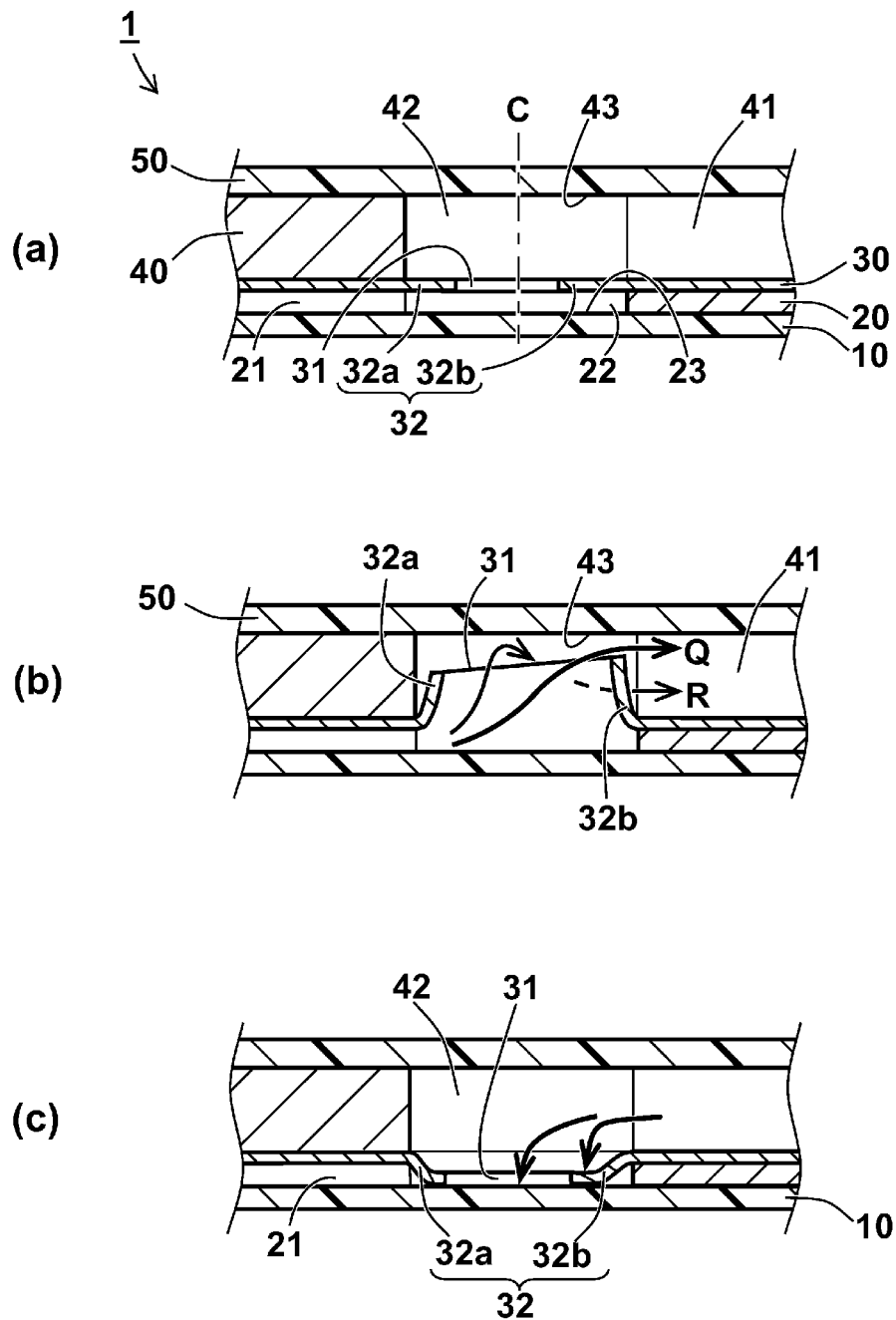
FIG. 1 is a schematic cross-sectional view of the check-valve according to the present invention.

Hereunder, embodiments to practice the present invention in detail will be explained, but the scope of the present invention is not restricted by these embodiments.

A cross-sectional view of check-valve 1 according to the present invention is shown in FIG. 1(a). The check-valve 1 has a thin sheet 20 and a thick sheet 40 which are a valve chamber forming member, a partition sheet 30 sandwiched between the thin sheet 20 and the thick sheet 40, and a base sheet 10 and a covering sheet 50 which are bonded to outermost parts of the thin sheet 20 and the thick sheet 40, respectively. The sheets 10, 20, 30, 40, 50 are stacked in this order and integrated.

The base sheet 10 and the covering sheet 50 are made from a hard cycloolefin resin. The thin sheet 20, the partition sheet 30 and thick sheet 40 are made from a silicone rubber having flexibility and elasticity, sandwiched between the base sheet 10 and the covering sheet 50, and supported thereby.

In the check-valve 1, a flow-in valve chamber 22 which penetrates the thin sheet 20 and sandwiched between the base sheet 10 and the partition sheet 30 is formed. The base sheet 10 faces the partition sheet 30 in a cavity of the flow-in valve chamber 22, and forms a bottom surface 23 which is a part of the inner face of the flow-in valve chamber 22. In addition, a flow-out valve chamber 42, which penetrates the thick sheet 40 and is sandwiched between the partition sheet 30 and covering sheet 50, is formed. The covering sheet 50 faces the partition sheet 30 in a cavity of the flow-out valve chamber 42 and forms a upper surface 43 which is a part of the inner face of the flow-out valve chamber 42. The both valve chambers 22, 42 have a concentric cylindrical shape having same radius. The both valve chambers 22, 42 have the radius somewhat larger than a width of flow paths 21, 41, and are overlapped (see FIG. 4(a)). A depth of the flow-in valve chamber 22 equals a thickness of the thin sheet 20. A depth of the flow-out valve chamber 42 equals a thickness of the thick sheet 40. Therefore the flow-in valve chamber 22 is shallower than the flow-out valve chamber 42.

A through-pass hole 31 is opened in the partition sheet 30 by penetrating it. The flow-in valve chamber 22 and the flow-out valve chamber 42 communicate each other through it. The through-pass hole 31 has an elongated circular shape like an oval hole. Two sides of longitudinal direction in the elongate hole are parallel to the both flow paths 21, 41 in a plan view (see FIG. 4(a)). A center of the through-pass hole 31 is decentered from a central axis C of the both valve chambers 22, 42 having the cylindrical shape to a shallow flow path 21 side.

The partition sheet 30 has an inner flange 32 which projects so as to part the cylindrical cavity formed by the both valve chambers 22, 42 into the flow-in valve chamber 22 and the flow-out valve chamber 42. Because the partition sheet 30 is made from silicone rubber, the inner flange 32 has rich flexibility and softness. A width of the inner flange 32 does not represent a constant value, because the through-pass hole 31 has the elongated circular shape which is decentered from the central axis C of the both valve chambers 22, 42. The width of the inner flange 32 is narrow at a shallow flow path side inner flange 32a, and wide at a deep flow path side inner flange 32b. Projecting widths of the shallow flow path side inner flange 32a and the deep flow path side inner flange 32b are narrower than the thickness of the thick sheet 40 (i.e. a depth of the deep flow path 41), and wider than the thickness of the thin sheet 20 (i.e. a depth of the shallow flow path 21).

In the check-valve 1, the shallow flow path 21, which penetrates the thin sheet 20 and is sandwiched between the base sheet 10 and partition sheet 30, is formed. The deep flow path 41, which penetrates the thick sheet 40 and is sandwiched between the covering sheet 50 and the partition sheet 30, is formed therein. One end of the shallow flow path 21 is connected to the flow-in valve chamber 22. One end of the deep flow path 41 is connected to the flow-out valve chamber 42.

FIG. 1(b) shows a scene where fluid flows through the check-valve 1 in a direction of the normal flow. In FIG. 1(b), arrows Q, R indicate a flow of the fluid. The fluid is liquid or gas. By pressure of the fluid which flows form the shallow flow path 21 into the flow-in valve chamber 22, the inner flange 32 is flexed so as to heave from an edge thereof to the flow-out valve chamber 42. The width of the inner flange 32 is narrower than the thickness of the thick sheet 40. Thereby even when the inner flange 32 is flexed toward the flow-out valve chamber 42, the inner flange 32 does not contact to the upper surface 43 of the flow-out valve chamber 42 and thus, the flow-out valve chamber 42 is not occluded. In the result, the check-valve 1 becomes in an open state. The fluid is flowed into the flow-out valve chamber 42 through the through-pass hole 31, further passed interspace between the deep flow path side inner flange 32b and the upper surface 43 and finally flowed out to the deep flow path 41 (Route Q).

An opening face of the through-pass hole 31 is somewhat tilted with respect to the upper surface 43 by a difference of the respective widths of the deep flow path side inner flange 32b and the shallow flow path side inner flange 32a. When the fluid having a high pressure e.g. 100 to 200 kPa, higher than 200 kPa, is flowed into the both valve chambers 22, 42, a part of the wide deep flow path side inner flange 32b, which is received the high pressure, is elongated due to the elasticity of the silicone rubber. The interspace between the deep flow path side inner flange 32b and the upper surface 43 therefore is tiny. In this case the fluid can be smoothly flowed out to the deep flow path 41 through the shallow flow path side inner flange 32a side of the through-pass hole 31 and lateral parts of the through-pass hole 31 (Route R).

FIG. 1(c) shows a scene where the fluid flows into the flow-out valve chamber 42 of the check-valve 1. The inner flange 32 is flexed to the flow-in valve chamber 22 by the pressure of the fluid. Since the width of the inner flange 32 is wider than the thickness of the thin sheet 20, the inner flange 32 is contacted to the bottom surface 23 of the flow-in valve chamber 22. Further the inner flange 32 is pressurized by the pressure of the fluid and sunk in like a dish shape. A face around the through-pass hole 31 in the inner flange 32 and the bottom surface 23 are contacted. Thereby the flow-in valve chamber 22 is completely occluded, and then the check-valve 1 becomes a closed state. In the result the fluid cannot be flowed into the shallow flow path 21. The deep flow path side inner flange 32b locating the deep flow path 41 side is easily received a reverse pressure, which is generated by a reverse flow of the fluid, depending on having the width wider than that of the shallow flow path side inner flange 32a. Thereby the deep flow path side inner flange 32b is flexed to the flow-in valve chamber 22 side by the reverse flow, and further whole of the inner flange 32b is quickly flexed. Consequently the flow-in valve chamber 22 is occluded by the inner flange 32, and the fluid which flows in reverse is not leaked and quickly stopped.

As just described, the check-valve 1 has the inner flange 32, which projects in the both valve chambers 22, 42 while having the width corresponding the depth difference between the flow-in valve chamber 22 and the flow-out valve chamber 42, and the through-pass hole 31 opened at the partition sheet 30. According to the check-vale 1, the fluid of the normal flow from the shallow flow path 21 to the deep flow path 41 therefore can be smoothly flowed, and the fluid of the reverse flow from the deep flow path 41 to the shallow flow path 21 can be reliably stopped. The check-valve 1 has a simple structure of which the partition sheet 30 is sandwiched between the thin sheet 20 and the thick sheet 40 which is the valve chamber forming member. The fluid works as a motive power source which works the inner flange 32. Because the motive power source such as a pump and a piezoelectric element for directly pressurizing/depressurizing the flow-in valve chamber 22 from the above is not required, the check-vale 1 can be quickly and easily produced with a low cost.

Since the partition sheet 30 is made from the silicone rubber, the check-valve 1 has the superior elasticity and flexibility. The inner flange 32 can be lithely flexed, even if under severe conditions such as generating the reverse pressure at a short cycle e.g. the fluid having a pulse. The open state or the closed state thereof may be instantly switched in accordance with the flow of the fluid. According to the check-valve 1, because the inner flange 32 can stop the reverse flow by a simple behavior as slightly flexing thereof, the volume of the both valve chambers 22, 42 can be small, and the check-valve 1 is thin and compact.

Hardness and the thickness of the silicone rubber for producing the inner flange 30 is suitably determined depending on the pressure and viscosity of the fluid. Not especially restricted, the hardness in Shore-A hardness is preferably from 20 to 70, more preferably from 30 to 70 and even more preferably from 30 to 60. The thickness is preferably from 20.0 to 200 μm, more preferably from 30.0 to 150 μm and even more preferably from 30.0 to 100 μm. When the hardness and the thickness of the partition sheet 30 are smaller than the above ranges, the inner flange 32 is easily elongated and excessively flexed by the pressure of the normal flow and thus, the flow-out valve chamber 42 is occluded. When these are larger than the above ranges, the inner flange 32 is difficulty flexed and thus, the reverse flow cannot be stopped. The hardness of the silicone rubber may be measured in accordance with Japanese Industrial Standard K6253.

Figure 2:
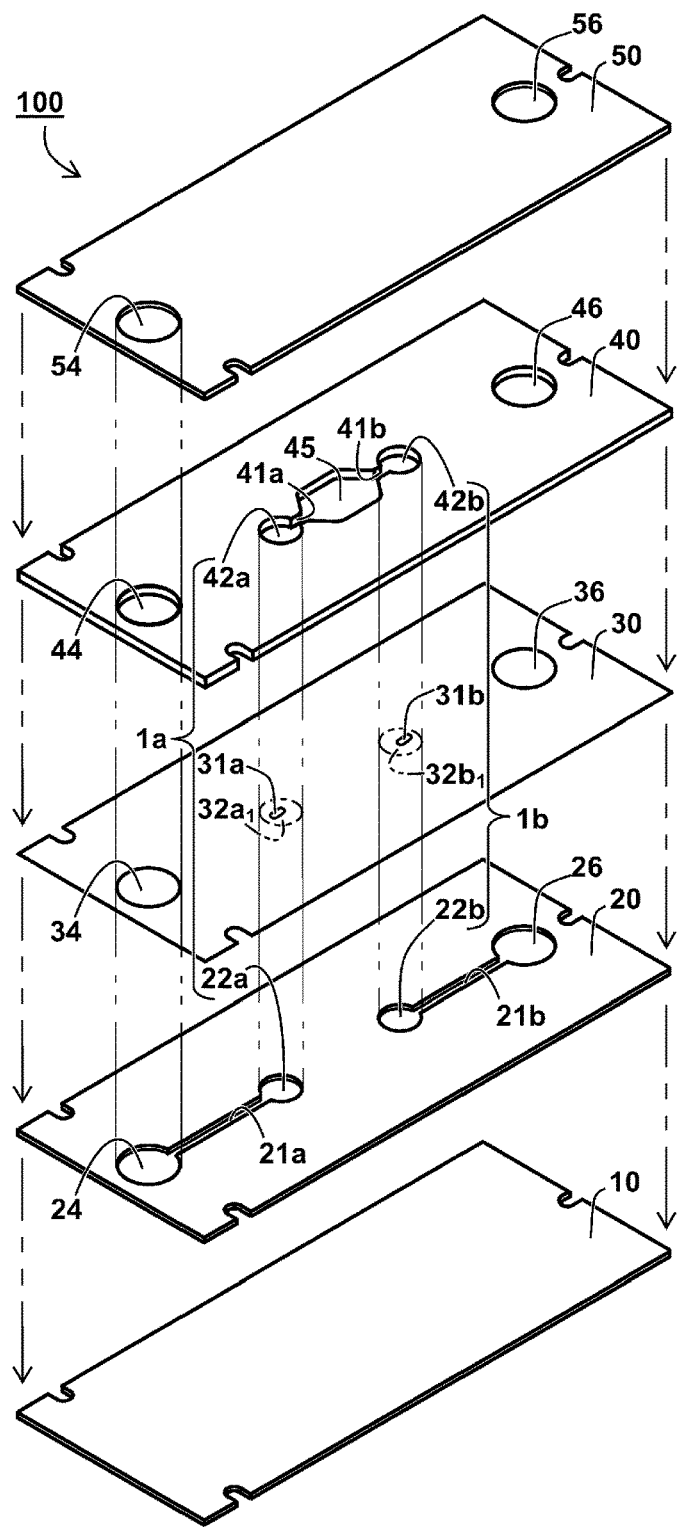
FIG. 2 is a schematic exploded perspective view of the microchemical chip according to the present invention.

The check-valve 1 is suitably used by being set in a microchemical chip. A microchemical chip 100 of the present invention having the check-valve 1 is shown in FIG. 2. In the microchemical chip 100, the base sheet 10, the thin sheet 20, the partition sheet 30, the thick sheet 40 having a reaction cistern 45, and the covering sheet 50 are stacked and bonded. The microchemical chip 100 is used by being mounted in a microreactor (not shown).

The microchemical chip 100 is used in a real-time PCR amplification (polymerase chain reaction amplification) in order to measure an amplification amount of nucleic acid by measuring fluorescence emitted after synthesis of the nucleic acid having double-strand such as DNA in the reaction cistern 45. The microchemical chip 100 is called a PCR chip. The microchemical chip 100 has the check-valve 1a in one side of the reaction cistern 45 and the check-valve 1b in the other side thereof. The reaction cistern 45 is sandwiched between the check-valve 1a and the check-valve 1b. The check-valve 1b works as an air vent valve which emit air trapped in the reaction cistern 45 etc.

The shallow flow path 21 is extended from a liquid specimen pumping start part 24 to a flow-in valve chamber 22a of the check-valve 1a. The liquid specimen pumping start part 24 is communicated with a liquid specimen inlet 54, which is connected to external side, through communicating holes 34, 44. The liquid specimen, in which a substrate (deoxynucleotide), a buffer solution, an enzyme (polymerase), template DNA, a primer and a fluorescent substance (intercalator) are mixed, is injected from the liquid specimen inlet 54.

The flow-out valve chamber 42a of the check-valve 1a is communicated with the reaction cistern 45 through the deep flow path 41a. The reaction cistern 45 is communicated with the flow-out valve chamber 42b of the check-valve 1b through a deep flow path 41b. The flow-in valve chamber 22b of the check-valve 1b is communicated with a flow-out part 26 through the shallow flow path 21b. The flow-out part 26 is communicated with a liquid specimen outlet 56, which is connected to external side, via through-pass holes 36, 46.

Figure 3:
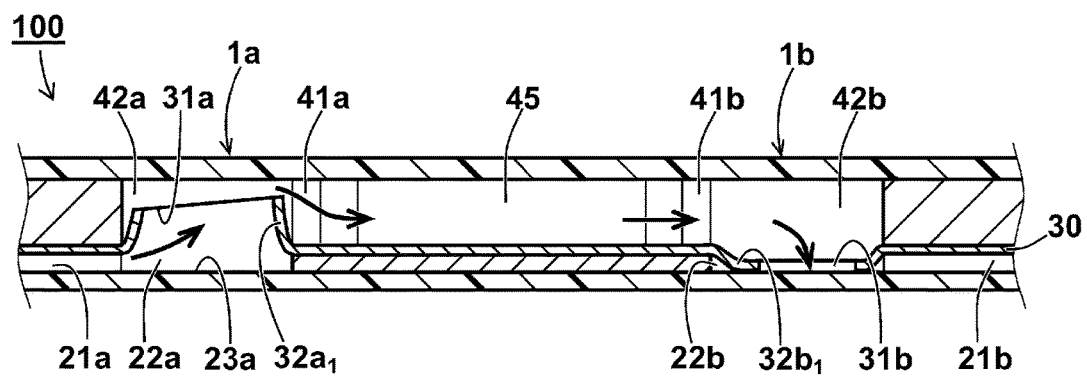
FIG. 3 is a schematic partially cross-sectional view of the microchemical chip according to the present invention.

FIG. 3 shows a partially cross-sectional view of the microchemical chip 100 shown in FIG. 2. In FIG. 3, the flow of the fluid is shown by heavy solid arrows. The liquid specimen, which is injected from the liquid specimen inlet 54 while being pressurized by a supplying pump of a microreactor, is arrived the liquid specimen pumping start part 24 through the communicating holes 34, 44 (see FIG. 2). The liquid specimen further flows in the shallow flow path 21a, and is arrived the flow-in valve chamber 22a of the check-valve 1a. The inner flange 32a₁ is flexed toward the flow-out valve chamber 42a side by the flow of the liquid specimen and thus, the check-valve 1a becomes in the open state. The liquid specimen is passed the through-pass hole 31a, and arrived the reaction cistern 45 through the flow-out valve chamber 42a and the deep flow path 41a. Since the liquid specimen is flowed by being pressurized, air, which is trapped in the respective flow paths 21a, 41a, the both valve chamber 22a, 42a and the reaction cistern 45, is extruded and sent toward the deep flow path 41b and the flow-out valve chamber 42b.

Furthermore, since the liquid specimen is flowed into the deep flow path 41b, the air is sent to the flow-out valve chamber 42b of the check-valve 1b which is an air vent valve. The liquid specimen is flowed toward the flow-out valve chamber 42b of the check-valve 1b through the deep flow path 41a, the reaction cistern 45 and the deep flow path 41b. Thereby, the air trapped therein is extruded ahead to the flow of the liquid specimen. The inner flange 32b₁ is not flexed by slight pressure which is generated by the extruded air and thus, the open state of the check-valve 1b can be maintained. Therefore the air is passed via a through-pass hole 31b, flowed into the flow-in valve chamber 22b, the shallow flow path 21b and the flow-out part 26 in this order, and finally emitted from the outlet 56 through communicating holes 36, 46.

The inner flange 32b₁ is barely flexed toward the flow-in valve chamber 22b side by the pressure of the liquid specimen flowed into the flow-out valve chamber 42b, and finally contacted with the base sheet 10. The check-vale 1b therefore becomes in the closed state. The liquid specimen cannot be flowed out to the shallow flow path 21b. Thereby the liquid specimen, which is continuously injected from the liquid specimen inlet 54 to the shallow flow path 21a, is held in the flow-out valve chamber 42b, the deep flow path 41b and the reaction cistern 45 in this order. When the liquid specimen is flowed from the reaction cistern 45 to the flow-out valve chamber 42, the inner flange 32a₁ of the check-valve 1a is tightly contacted with the bottom surface 23a by being flexed toward the flow-in valve chamber 22a side and thus, the flow-in valve chamber 22a is occluded. Thereby the check-valve becomes in the closed state. The liquid specimen cannot be reversed to the shallow flow path 21a, and is held in the microchemical chip 100.

When the hardness and the thickness of the partition sheet 30 are ranged within the above, the inner flanges 32a₁, 32b₁ can be set so as to be started to flex by optional pressure. The inner flanges 32a₁, 32b₁ are preferably started to flex at 30 kPa or less. When the inner flanges 32a₁, 32b₁ are flexed by lower pressure than this range, the air cannot be emitted. When the inner flanges 32a₁, 32b₁ cannot be flexed by larger pressure than this range, the liquid specimen is flowed out toward the shallow flow paths 21a, 21b through the through-pass holes 31a, 31b.

For example, the liquid specimen in the reaction cistern 45 is heated and cooled on the microreactor as follows. First, the liquid specimen is heated from a room temperature to 94° C. A denaturation reaction which separates double-strand DNA into single-strand is occurred. In this case, when pressure in the reaction cistern 45 is increased by heating, the liquid specimen is not leaked from the microchemical chip 100 because the reverse flow of the liquid specimen is prevented by the check-valves 1a, 1b. Next, the liquid specimen is cooled at 40 to 60° C., and an annealing reaction is occurred. The single-strand DNA and a primer are bonded by an annealing reaction. Finally, when the liquid specimen is heated at 60 to 70° C., the primer bonded with the single-strand DNA is elongated by a polymerase. By the heating and cooling are repeated, DNA is amplified. Amount of this amplification is measured by detecting fluorescent intensity of an intercalator. After the measurement thereof, the microchemical chip 100 is thrown away without ejecting the liquid specimen.

Incidentally, an amplification of RNA is conducted as follows. RT-PCR (reverse transcription) of single-strand RNA is conducted, cDNA is synthesized, and then operation of the PCR amplification is conducted in the same manner as DNA.

As just described, because the microchemical chip 100 has at least the two check-valves 1, namely the check-valve 1a which stops the reverse flow and the check-valve 1b which is the air vent valve for emitting the trapped air in the reaction cistern 45 etc., the reaction cistern 45 can be filled with the mixed solution of the liquid specimen and the fluorescent solution while the trapped air in the reaction cistern 45 etc. can be emitted. Furthermore, according to the microchemical chip 100, the reverse flow of the liquid specimen etc. which fills the reaction cistern 45 can be stopped. The liquid specimen and the mixed solution injected into the microchemical chip 100 therefore are not leaked therefrom.

Moreover, the liquid specimen is injected from the liquid specimen inlet 54 at a specific amount by using a pipette, and then may be pumped to the reaction cistern 45 by gas such as compressed gas which does not interfere the measurement of the nucleic acid amplification, or by flowing in liquid such as physiological saline which is pressurized from the liquid specimen inlet 54.

The thicknesses of the thin sheet 20, thick sheet 40, the base sheet 10 and the covering sheet 50 are optionally designed corresponding to the shape of the microchemical chip 100 having the check-valve 1 and usage thereof. The thick sheet 40 preferably has the thickness thicker than the thin sheet 20. Further the projecting width of the inner flange 32 is preferably wider than the thickness of the thin sheet 20 and narrower than the thick sheet 40. For instance, in the check-valve 1, the base sheet 10 has the thickness from 40.0 µm to 3.00 mm, the thin sheet 20 has the thickness from 30.0 to 200 µm, the partition sheet 30 has the thickness from 20.0 to 200 µm, the thick sheet 40 has the thickness from 200 µm to 3.00 mm, and the covering sheet 50 has the thickness 40.0 µm to 3.00 mm.

The microchemical chip 100 which has the check-valve 1 is produced as follows. A resin plate for preparing the base sheet 10 and the covering sheet 50 is cut out so as to have a desired size and shape. Active groups are generated on the upper side of the base sheet 10 and the lower side of the covering sheet 50 by conducting a corona discharge through a discharge tube.

The thin sheet 20 is provided with the shallow flow paths 21a, 21b, the flow-in valve chambers 22a, 22b, the liquid specimen pumping start part 24 and the flow-out part 26 by punching or using a laser cutter. In the same manner as this, the partition sheet 30 is provided with the through-pass holes 31a, 31b and the communicating holes 34, 36, the thick sheet 40 is provided with the deep flow paths 41a, 41b, the flow-out valve chambers 42a, 42b, the communicating holes 44, 46 and the reaction cistern 45, and the covering sheet 50 is provided with the liquid specimen inlet 54 and the outlet 56. The active groups are generated on the both sides of the thin sheet 20, the partition sheet 30 and the thick sheet 40 by conducting the corona discharge through the discharge tube.

Next, while notches bored at the circumference of the respective sheets 10, 20, 30, 40, 50 are fitted in projections which are raised on a jig, the all sheets 10, 20, 30, 40, 50 are stacked. In accordance with this process, the respective sheets 10, 20, 30, 40, 50 are aligned so that the through-pass hole 31a is positioned in the both valve chambers 22a, 42a while the flow-in valve chamber 22a and the flow-out valve chamber 42a are overlapped, so that the through-pass hole 31b is positioned in the both valve chambers 22b, 42b while the flow-in valve chamber 22b and the flow-out valve chamber 42b are overlapped, so that the liquid specimen pumping start part 24, the communicating holes 34, 44 and the liquid specimen inlet 54 are overlapped, and so that the flow-out part 26, communicating holes 36, 46 and the outlet 56 are overlapped. The stacked sheet 10, 20, 30, 40, 50 are compressed while heating. The active groups such as hydroxy groups, which are generated on surface of the respective sheets 10, 20, 30, 40, 50 by the corona discharge, are reacted through dehydration reaction therebetween. Ether groups which are covalent bonds are formed by the dehydration reaction of the active groups and thus, the sheet 10, 20, 30, 40, 50 are bonded. As just described, the check-valve 1 is obtained.

Figure 4:
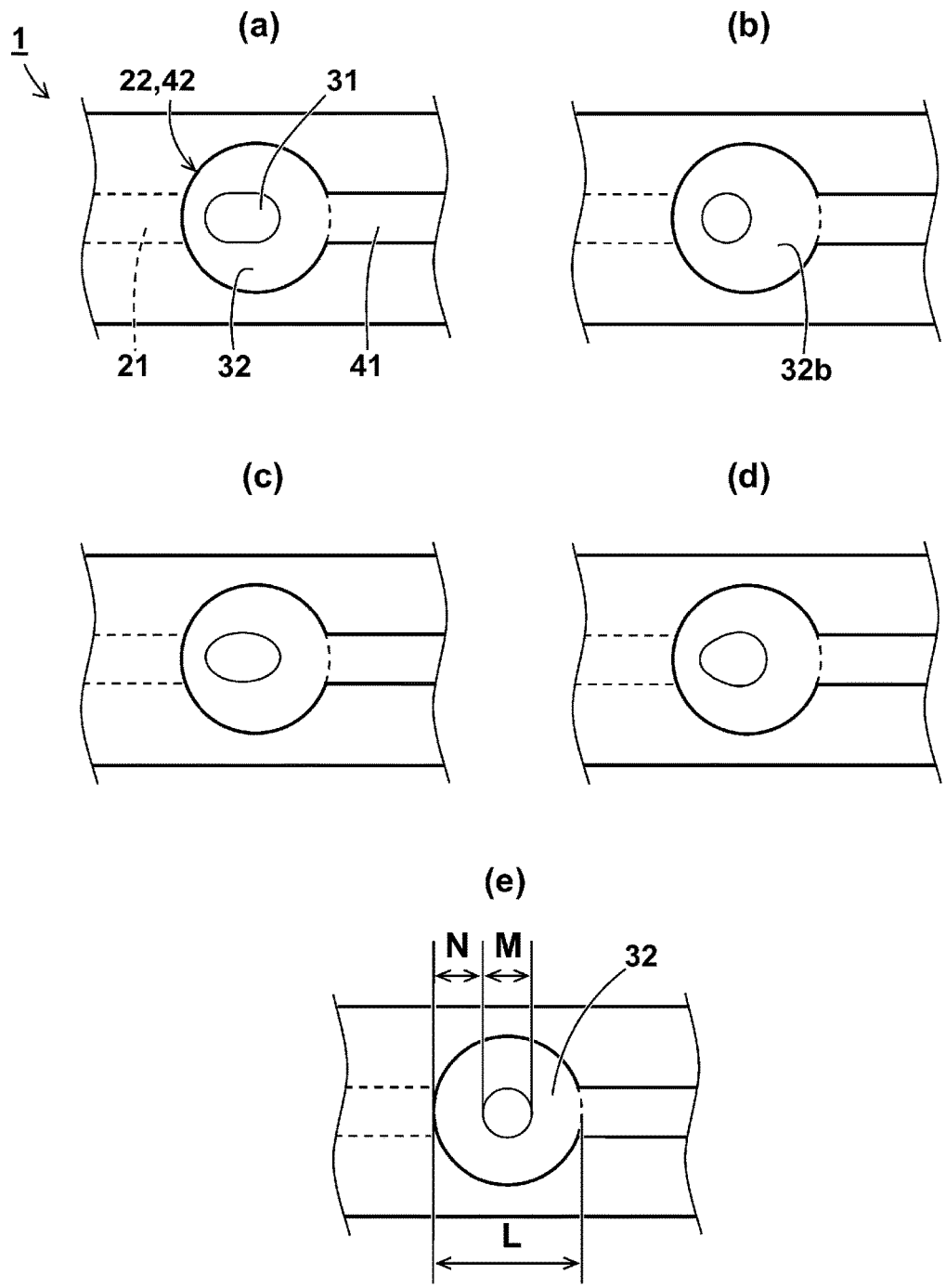
FIG. 4 is a schematic plan view of the check-valve according to the present invention.

A schematic plan view of the thick sheet 40, the partition sheet 30 and the thin sheet 20 in the check-valve 1 is shown in FIG. 4. In FIG. 4, the thick sheet 40 is shown by heavy solid lines, the partition sheet 30 is shown by thin solid line, and the thin sheet 20 is shown by broken lines. As shown in FIG. 4(a), when through-pass hole 31 has the elongated circular shape having long sides which are in parallel with the both flow paths 21, 41 and short sides having same width as the both flow paths 21, 41, resistance of the fluid which passes the through-pass hole 31 may be decreased. Accordingly the fluid may be smoothly flowed. Further, as shown in FIG. 4(b), when the through-pass hole 31 has a circular shape having a same diameter as the width of the both flow paths 21, 41, the width of the deep flow path side inner flange 32b is wide compared with the through-pass hole 31 having the elongated circular shape. The reverse flow directing to the shallow flow path 21 can be stopped without fail. As the shape of the through-pass hole 31, an oval shape shown in FIG. 4(c) and an egg shape shown in FIG. 4(d) are included. The shape and the diameter of the through-pass hole 31 may be optionally designed corresponding to kind of the fluid and viscosity thereof.

The center of the through-pass hole 31 and the central axis C of the both valve chamber 22, 42 may be coaxial (see FIG. 1). FIG. 4(e) shows an embodiment of which the through-pass hole 31 is formed in concentric circular shape with the both valve chambers 22, 42. For example, according to the check-valve 1 having the both valve chambers 22, 42 of 3 mm diameter L, the through-pass hole 31 of 1 mm diameter M, the inner flange of 1 mm width N, the thick sheet 40 of 400 μm thickness and the thin sheet 20 of 100 μm thickness, the reverse flow can be more reliably stopped because the width of the inner flange 32 is enough wider than the thickness of the thin sheet 20. The check-valve 1 is preferably used in flowing the fluid having comparably low pressure such as less than 40 kPa. In the low pressure condition, the inner flange 32 is not flexed and elongated toward the flow-out valve chamber 42 excessively. Thereby when the width of the inner flange 32 is wider than the thickness of the thick sheet 40, the flow-out valve chamber 42 is not occluded by the inner flange 32 and thus, the fluid can be flowed with the normal flow direction.

A through-pass part may be a slit 33 cut into the inner flange 32 instead of the through-pass hole 31, as shown in FIG. 5(a). The slit 33 is cut into the central part of the inner flange 32 so as to be a parallel line to the respective flow paths 21, 41. As shown in FIG. 5(b), the slit 33 is opened by pressure of the fluid (a heavy broken line therein) which is flowed from the shallow flow path 21 into the flow-in valve chamber 21, and then the fluid is flowed from the flow-out valve chamber 42 toward the deep flow path 41 (a heavy solid line therein). When the through-pass part is the slit 33, a slit is enough to be formed to the partition sheet 30 in order to form the through-pass part. Therefore a process of forming the through-pass part may be simplified and thus, the check-valve 1 can be quickly and easily produced.

Figure 5:
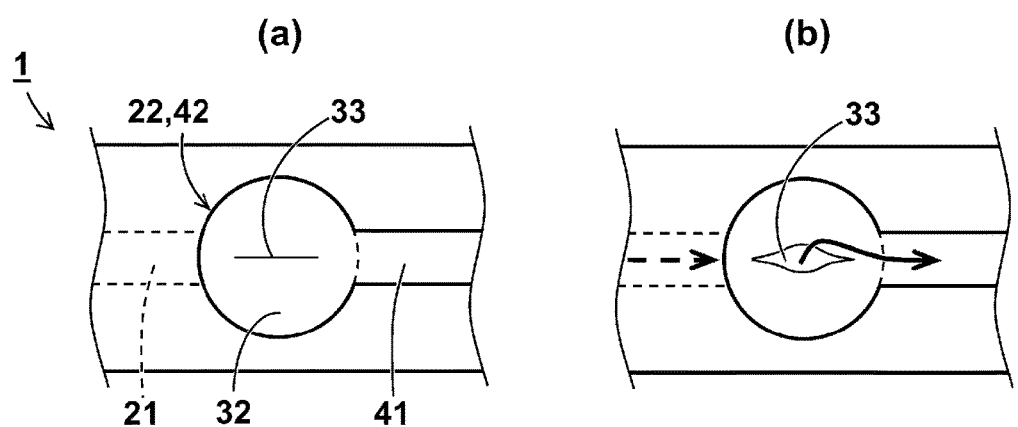
FIG. 5 is a schematic plan view of the other check-valve according to the present invention.
Figure 6:
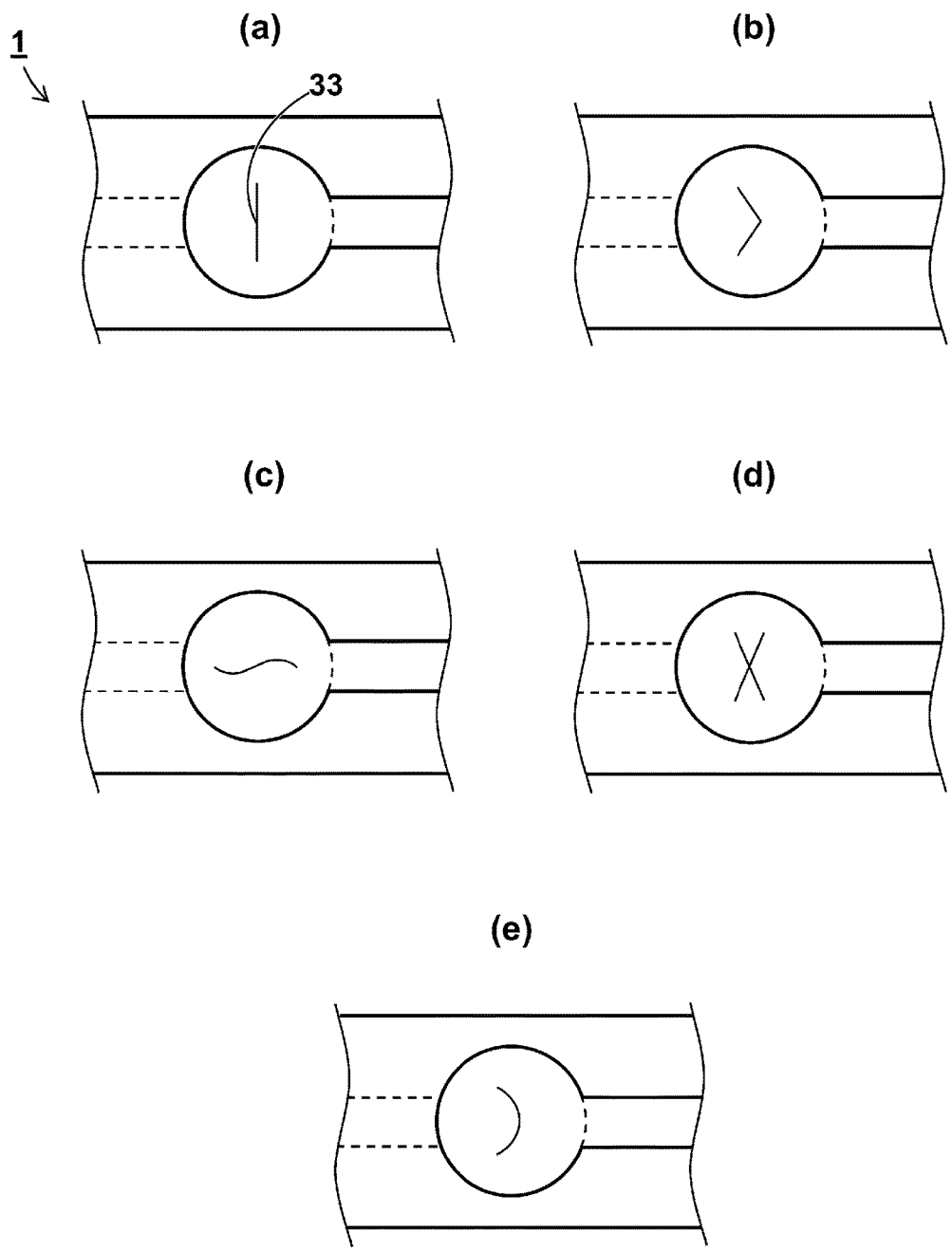
FIG. 6 is a schematic plan view of the other check-valve according to the present invention.

In addition to the slit 33 shown in FIG. 5, the slit 33 may have a straight line shape which is cut with a perpendicular direction relative to the respective flow paths 21, 41 as shown in FIG. 6(a), a V-shape as shown in FIG. 6(b), a wave shape as shown in FIG. 6(c), a cross shape as shown in FIG. 6(d) and an approximate U-shape as shown in FIG. 6(e). The shape of the slit 33 is optionally selected corresponding to the viscosity and the pressure of the fluid.

Figure 7:
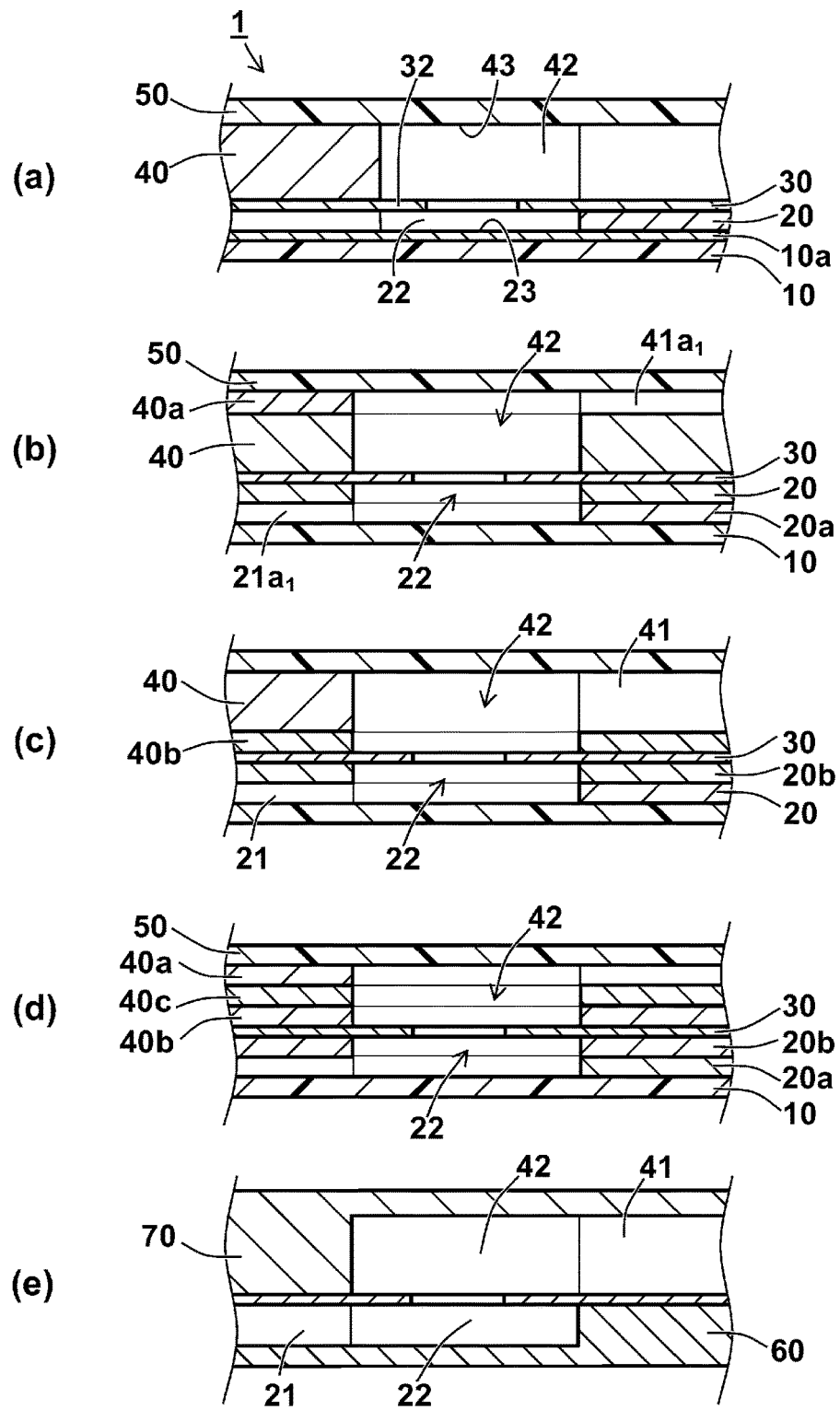
FIG. 7 is a schematic cross-sectional view of the other check-valve according to the present invention.

The other embodiment of the check-valve 1 is shown in FIG. 7. The fluid which is flowed in the check-valve 1 shown in FIG. 7(a) is liquid. The check-valve 1 has a water repellent sheet 10a sandwiched between the base sheet 10 and the thin sheet 20 and bonded thereto. The water repellent sheet 10a is made from a silicone rubber. The water repellent sheet 10a has the same shape as the base sheet 10 except of the thickness. A part of the water repellent sheet 10a is exposed at the flow-in valve chamber 22. The bottom surface 23 is formed by the part of the water repellent sheet 10a. The covering sheet 50 which forms the upper surface 43 is made from a cycloolefin resin. Because the silicone rubber has water repellency, wettability thereof with the liquid is lower than that of the cycloolefin resin. Therefore a contact angle between the liquid and the bottom surface 23 of the flow-in valve chamber 22 is larger than that between the liquid and the upper surface 43 of the flow-out valve chamber 42.

The inner flange 32, which is flexed toward the flow-in valve chamber 22 by the reverse flow of the liquid, is contacted to the bottom surface 23 and occludes the flow-in valve chamber 22 (see FIG. 1(c)). Because the bottom surface 23 which repels the liquid by having the low water repellency can be tightly contacted with the inner flange 32, the liquid which is reversely flowed is not leaked from the check-valve 1. In the result the reverse flow of the liquid can be more reliably stopped. Incidentally, the silicone rubber for forming the water repellent sheet 10a may be same as the partition sheet 30, or alternatively may be different therefrom. Furthermore, the bottom surface 23 may be provided with the water repellency by conducting a water repellent finishing to the base sheet 10.

The contact angle between the liquid and the upper surface 43 may be additionally decreased by conducting a hydrophilic finishing to the upper surface 43 of the flow-out valve chamber 42. According to the hydrophilic finishing, the wettability between the upper surface 43 and the liquid is increased. Even when the inner flange 32 which is elongated by the liquid flowed with the high pressure is contacted to the upper surface 43 of the flow-out valve chamber 42, the liquid is easily passed the interspace between the inner flange 32 and the upper surface 43. Thereby the depth of the flow-out valve chamber 42 can be same as that of the flow-in valve chamber 22. In the result, for the valve chamber forming member for producing the both sheets 20, 40, the same thickness thereof can be used.

As the hydrophilic finishing, for example, a corona discharge treatment and a coating treatment using a hydrophilic substance are exemplified. In addition, the upper surface 43 may be a fine concave-convex surface by conducting a blast finishing. Since the elongated inner flange 32 is not tightly contacted to the upper surface 43, the liquid can be smoothly flowed along the concave parts of the upper surface 43. Moreover, by a hydrophilic sheet (not shown) having the same shape as the covering sheet 50 is sandwiched between the thick sheet 40 and the covering sheet 50 and bonded thereto, the upper surface 43 may have hydrophilic property. When the bottom surface 23 of the flow-in valve chamber 22 and the upper surface 43 of the flow-out valve chamber 42 have the water repellency or the hydrophilic property, respectively, so that the contact angles between these surfaces and the liquid are mutually different, the liquid is more smoothly flowed in the check-valve 1 with the normal flow and the reverse flow is more reliably stopped.

In the check-valve 1 shown in FIG. 7(b), the thin sheet 20 and the thick sheet 40 do not have the flow paths. A flow path sheet 20a having the flow path $21a_1$ between the thin sheet 20 and the base sheet 10 is bonded thereto. A flow path sheet 40a having the flow path $41a_1$ between the thick sheet 40 and the covering sheet 50 is bonded thereto. The flow-in valve chamber 22 is formed by penetrating the thin sheet 20 and the flow path sheet 20a. The flow-out valve chamber 42 is formed by penetrating the thick sheet 40 and the flow path sheet 40a. The both flow path sheets 20a, 40a have the same thickness. According to such the structure, even when the respective flow paths $21a_1$, $41a_1$ have the same depth by the flow path sheets 20a, 40a which have the same thickness, the check-valve 1 can be formed.

In the check-valve 1 shown in FIG. 7(c), a valve chamber forming sheet 20b between the thin sheet 20 having the flow path 21 and the partition sheet 30 is bonded thereto. A valve chamber forming sheet 40b between the thick sheet 40 and the partition sheet 30 is bonded thereto. The flow-in valve chamber 22 is formed by penetrating the thin sheet 20 and the valve chamber forming sheet 20b. The flow-out valve chamber 42 is formed by penetrating the thick sheet 40 and the valve chamber forming sheet 40b. The valve chamber forming sheets 20b, 40b have the same thickness. According to such the structure, because the respective flow paths 21, 41 and the both valve chambers 22, 42 are formed into the different sheets respectively, a process of forming these can be simplified.

The check-valve 1 shown in FIG. 7(d) does not have the thin sheet 20 and the thick sheet 40. The base sheet 10, the flow path sheet 20a, the valve chamber forming sheet 20b, the partition sheet 30, the valve chamber forming sheet 40b, a spacer sheet 40c, the flow path sheet 40a and the covering sheet 50 are stacked in this order. These adjacent sheets are mutually bonded. The flow-in valve chamber 22 is formed by penetrating the flow path sheet 20a and the valve chamber forming sheet 20b. The flow-out valve chamber 42 is formed by penetrating the valve chamber forming sheet 40b, the spacer sheet 40c and the flow path sheet 40a. The respective flow path sheets 20a, 40a, the respective valve chamber forming sheets 20b, 40b and the spacer sheet 40c mutually have the same thickness. The check-valve 1 has the spacer sheet 40c. Thereby, even when the sheets having the same thickness are stacked, the flow-out valve chamber 42 having the depth which is deeper than the flow-in valve chamber 22 can be formed. According to such the structure, because the thickness of the all sheets can be same except for the partition sheet 30, the check-valve 1 can be produced with low cost.

The valve chamber forming member of the check-valve 1 is not restricted to the above mentioned sheets. The check-valve 1 shown in FIG. 7(e) has a flow-in valve chamber forming member 60 and a flow-out valve chamber forming member 70. The shallow flow path 21 and the flow-in valve chamber 22 are formed into the flow-in valve chamber forming member 60 by engraving therewith. The deep flow path 41 and the flow-out valve chamber 42 are formed into the flow-out valve chamber forming member 70 by engraving therewith. The flow-in valve chamber forming member 60 and the flow-out valve chamber forming member 70 can be obtained as follows. A masking agent is applied on the valve chamber forming members 60, 70 except for regions for forming the respective flow paths 21, 41 etc. The respective flow paths 21, 41 etc. is formed by conducting an etching process, and then the masking agent is removed. Alternatively, a preform of a material is charged into a mold for forming the respective flow paths 21, 41 etc. According to such the structure, because the check-valve 1 can be produced by using only the three members namely, the both valve chamber forming members 60, 70 and the partition sheet 30, a cost of the production of the check-valve 1 can be reduced by reducing number of the members.

In the check-valve 1, a magnetic substance may be embedded and/or attached to the inner flange 32. Thereby the inner flange 32 is flexed corresponding to supplying magnetic force by a magnet from external side. The check-valve 1 can be switched between the open state and the closed state. As the magnetic substance, a ferromagnetic substance is preferably used. As the ferromagnetic substance, magnetic metal such as Fe, Ni and Co; magnetic metal oxides such as magnetite ($Fe_3O_4$), maghemite ($\gamma$-$Fe_2O_3$), magnetite-maghemite intermediate and iron-platinum alloy (FePt) are exemplified. Further, as the magnet, a neodymium magnet, an AlNiCo magnet, a samarium cobalt magnet or a ferrite magnet are exemplified. The magnetic substance and the magnet may be embedded into the inner flange 32, and may be attached thereto. Further the magnetic substance and the magnet may be attached the inner flange 32 by printing and applying. According to such the check-valve 1, the open state and the closed state can be optionally switched without depending on the pressure of the fluid.

Figure 8:
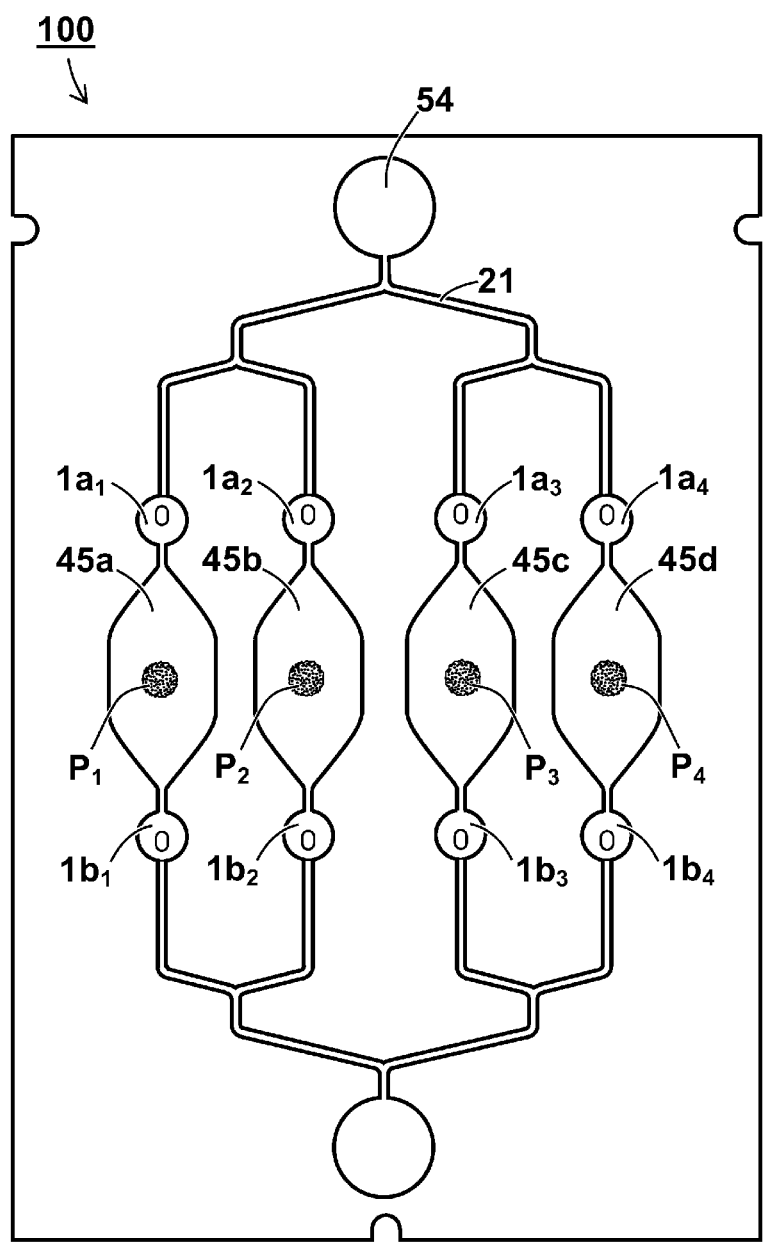
FIG. 8 is a schematic plan view of the other microchemical chip according to the present invention.

FIG. 8 shows a schematic plan view of the other microchemical chip 100 of the present invention. In FIG. 8, a pattern of the flow paths and the check-valves of the microchemical chip 100 is shown, and the structure of the steric flow paths etc. are omitted. The plural reaction cisterns

45a to 45d are paralleled in the single microchemical chip 100. The shallow flow path 21 branched from the liquid specimen inlet 54 like a tree diagram is reached to the reaction cisterns 45a to 45d through the check-valves 1a₁ to 1a₄, respectively. The reaction cisterns 45a to 45d are connected toward the check-valves 1b₁ to 1b₄ which are the air vent valves.

The powdered primers P₁ to P₄ are accommodated in the reaction cisterns 45a to 45d, respectively. Since a type of the primers P₁ to P₄ is mutually different. Mutually different gene loci are amplified in the reaction cisterns 45a to 45d by mixing the liquid specimen and the primers.

The liquid specimen which is a mixture of the deoxynucleotide, the buffer solution, the polymerase, the template DNA and the intercalator is injected from the liquid specimen inlet 54. When the liquid specimen is passed the branching points, and is flowed while being divided accordingly, and then further flowed toward the reaction cisterns 45a to 45d. The air in the reaction cisterns 45a to 45d is emitted through the check-valves 1b₁ to 1b₄ by the pressure of the liquid specimen. And then, since the check-valves 1b₁ to 1b₄ become in the closed state, the liquid specimen is held in the reaction cisterns 45a to 45d. In this case, amounts of the liquid specimen which is flowed toward the reaction cisterns 45a to 45d might be different because the liquid specimen does not equally divided at the branching point. Even when the amounts of the liquid specimen held in the reaction cisterns 45a to 45d might be different at one point in time, in response to the reaction cisterns 45a to 45d filled with the liquid specimen, the inner flanges of the check-valves 1a₁ to 1a₄ occlude the flow-in valve chambers which communicate to the shallow flow path 21. The liquid specimen is selectively flowed into the reaction cisterns 45a to 45d which are not still filled. The reaction cisterns 45a to 45d therefore are sequentially filled by the liquid specimen.

According to the microchemical chip 100, a total amount of the liquid specimen, which is required to fill the reaction cisterns 45a to 45d, is just injected from the liquid specimen inlet 54, and the liquid specimen can be equally divided. Thus, operation of PCR can be simplified, and the amplification amount of the nucleic acid can be quickly measured. Moreover because a mistake of the operation when dividing the liquid specimen is not occurred, the measurement can be precisely conducted.

Figure 9:
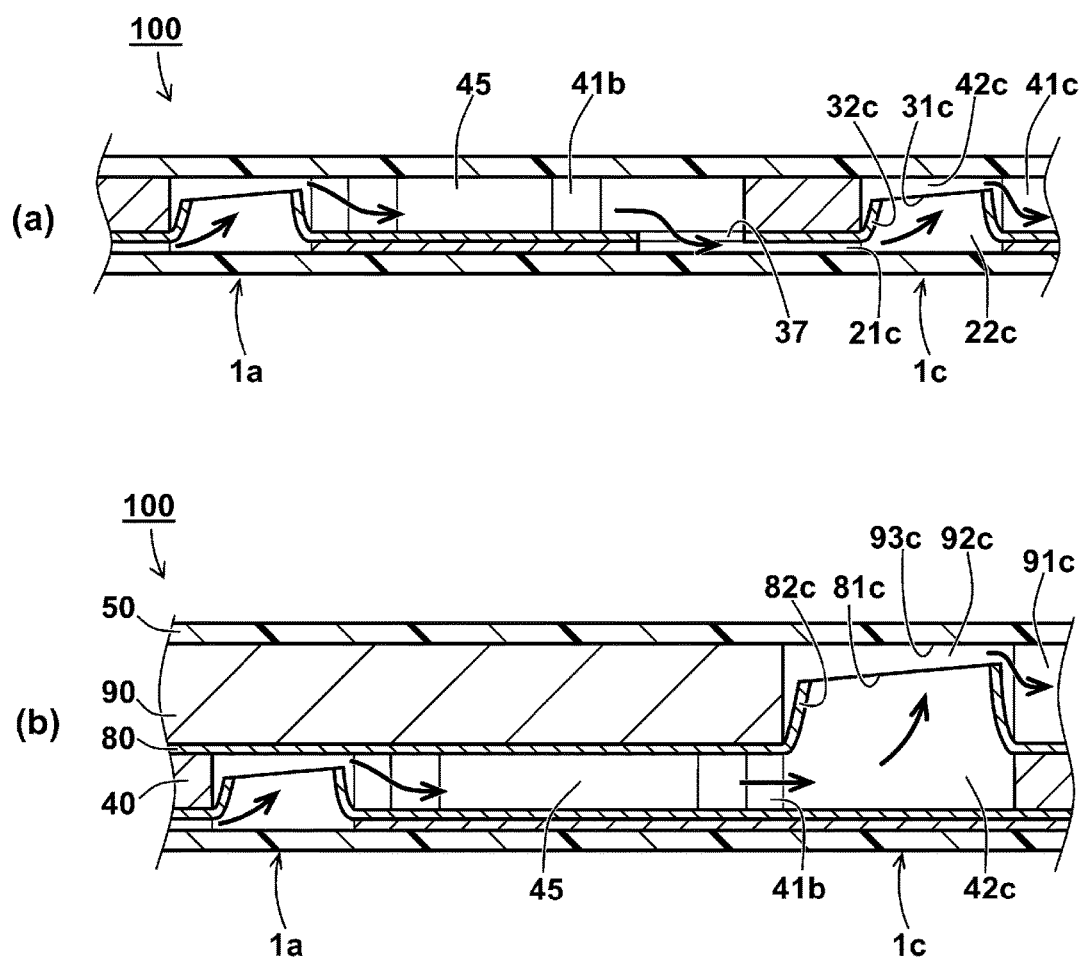
FIG. 9 is a schematic partially cross-sectional view of the other microchemical chip according to the present invention.

FIG. 9 shows a schematic cross-sectional view of the other microchemical chip 100 of the present invention. In FIG. 9(*a*), the flow of the fluid is shown by heavy solid arrow. The microchemical chip 100 shown in FIG. 9(*a*) has the check-valve 1c to flow the liquid specimen held in the reaction cistern 45. The flow-out valve chamber 42c of the check-valve 1c is communicated with the deep flow path 41c. The deep flow path 41c is communicated with the flow-out part 26, and further communicated with the outlet 56 connected to external side through the communicating holes 36, 46 (see FIG. 2). The flow-out valve chamber 22c of the check-valve 1c is communicated with the shallow flow path 21c. Furthermore the shallow flow path 21c is connected to the deep flow path 41b communicating with the reaction cistern 45 through the communicating hole 37 which is drilled the partition sheet 30.

Before the liquid specimen is held in the reaction cistern 45, a nozzle (not shown) connected to end of a gas pumping tube is inserted in the outlet 56 and fixed therewith. Compressed gas having pressure of more than 30 kPa is supplied from the deep flow path 41c to the check-valve 1c. Thereby since the inner flange 32c is flexed toward the flow-in valve chamber 22c and occludes it, the check-valve 1c becomes in the closed state. The liquid specimen injected from the liquid specimen inlet 54 (see FIG. 2) cannot be flowed from the check-valve 1c to the deep flow path 41c. The liquid specimen is held in the reaction cistern 45. Incidentally, when the check-valve 1c is the open state, the trapped air in the reaction cistern 45 is passed the check-valve 1c, the deep flow path 41c and the communicating holes 36, 46, and emitted from the outlet 56 by the pressure of the liquid specimen flowed into the microchemical chip 100. That is, the air can be emitted. In this case, when the reaction cistern 45 is filled by the liquid specimen, the check-valve 1c becomes the closed state by supplying the compressed gas from the outlet 56.

After the measurement of the amplification amount of the nucleic acid, the liquid specimen is discharged. By stopping the compressed gas supplied from the outlet 56, the check-valve 1c becomes in the open state. The liquid specimen passes the through-pass hole 31, flows the deep flow path 41c and finally arrives at the flow-out part 26 (see FIG. 2). The liquid specimen is ejected through the outlet 56. As needed, the ejection of the liquid specimen may be facilitated by supplying the compressed gas from the liquid specimen inlet 54.

As just described, when the microchemical chip 100 has the check-valves 1a, 1c which become both in the open state by corresponding to a flow direction (the normal flow direction) of the fluid such as the liquid specimen, the liquid specimen which was used after a reaction in the reaction cistern 45 can be ejected as needed.

FIG. 9(*b*) shows a schematic partially cross-sectional view of the microchemical chip 100 of the other embodiment. A second partition sheet 80 is further bonded onto an upper face side of the thick sheet 40, and a second thick sheet 90 having a thickness which is thicker than the thick sheet 40 is bonded onto an upper face side of the second partition sheet 80. The projecting width of the inner flange 82c of the check-valve 1c is wider than the thickness of the thick sheet 40 and narrower than the thickness of the second thick sheet 90. Thereby, when the inner flange 82c is flexed by the normal flow of the fluid, it is not contacted with the upper surface 93c of the flow-out valve chamber 92c. The flow-out valve chamber 92c is not occluded. The fluid can be passed the flow-out valve chamber 92c and flowed to the second deep flow path 91c. The microchemical chip 100 having the check-valve 1a, 1c which become both in the open state by corresponding to the normal flow direction of the fluid can be structured as well due to the second partition sheet 80 and the second thick sheet 90 being stacked between the thick sheet 40 and the covering sheet 50.

The respective sheets 10, 20, 30, 40, 50 may be bonded by the direct covalent bond, by the indirect covalent bond through a molecular adhesive such as a silane-coupling agent as a single molecular layer and by adhesion using an adhesive.

Functional groups in the molecules of the molecular adhesive are chemically reacted to form the covalent bond with adhesive articles. The molecular adhesive is directly or indirectly bonded to the adhesive articles through the covalent bond by molecular adhesive molecules of a single molecule or multiple molecules. The molecular adhesive is used for bonding the sheets 10, 20, 30, 40, 50. The two functional groups of the molecular adhesive form the covalent bond by chemically reacting with the respective sheets 10, 20, 30, 40, 50 which are the adhesive articles. The molecular adhesive means collectively ambifunctional molecules. Specifically various coupling agents including the silane-coupling agents are exemplified.

As the molecular adhesive, more specifically, a compound having an amino group such as triethoxysilylpropylamino-1,3,5-triazine-2,4-dithiol (TES), aminoethylaminopropyltrimethoxy silane;

a triazine compound having a trialkoxysilylalkylamino group such as a triethoxysilylpropylamino group and a mercapto group or an azide group, a triazine compound represented by Formula (1) as following, for example 2,6-diazido-4-{3-(triethoxysilyl)propylamino}-1,3,5-triazine (P-TES),

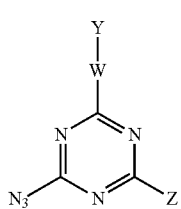

(1)

wherein W is a spacer group which for example may be the alkylene group or aminoalkylene group having optionally a substituted group or is directly bonded; Y is an OH group or a reactive functional group which generates an OH group by hydrolysis or cleavage e.g. the trialkoxyalkyl group; —Z is —$N_3$ or —$NR^1R^2$ ($R^1$ and $R^2$ are the same or different, and H or an alkyl group, —$R^3Si(R^4)_m(OR^5)_{3-m}$ [$R^3$ and $R^4$ are an alkyl group, $R^5$ is H or an alkyl group, m is 0 to 2]), incidentally, the alkylene group, alkoxy group and alkyl group are the chained, branched and/or cyclic hydrocarbon group having 1 to 12 carbon atoms which optionally has a substituted group; a thiol compound having a trialkoxysilylalkyl group;

an epoxy compound having a trialkyloxysilylalkyl group; a silane-coupling agent such as a vinylalkoxysiloxane polymer exemplified by $CH_2$=CH—Si($OCH_3$)$_2$—O—[Si($OCH_3$)$_2$—O-]$_n$-Si($OCH_3$)$_2$—CH=$CH_2$ (n=1.8 to 5.7) are included.

Furthermore as polysiloxane having a reactive group, a compound schematically represented by Formula (2) as following,

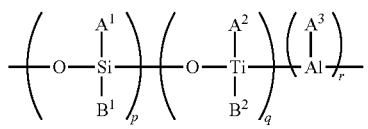

(2)

wherein p and q are a number of 0 or 2-200, and r is a number of 0 or 2-100 as p+q+r>2;
-$A^1$, -$A^2$ and -$A^3$ are either —$CH_3$, —$C_2H_5$, —CH=$CH_2$, —CH($CH_3$)$_2$, —$CH_2CH(CH_3)_2$, —C($CH_3$)$_3$, —$C_6H_5$ and/or —$C_6H_{12}$, or a reactive group which can be reacted with a hydroxy group wherein the reactive group is at least one selected from the group consisting of —$OCH_3$, —$OC_2H_5$, —OCH=$CH_2$, —OCH($CH_3$)$_2$, —$OCH_2CH(CH_3)_2$, —OC($CH_3$)$_3$, —$OC_6H_5$ and —$OC_6H_{12}$;
—$B^1$ and —$B^2$ are either —N($CH_3$)$COCH_3$ and/or —N($C_2H_5$)$COCH_3$, or a reactive group which can be reacted with a hydroxy group wherein the reactive group is at least one selected from the group consisting of —$OCH_3$, —$OC_2H_5$, —OCH=$CH_2$, —OCH($CH_3$)$_2$, —$OCH_2CH$($CH_3$)$_2$, —OC($CH_3$)$_3$, —$OC_6H_5$, —$OC_6H_{12}$, —$OCOCH_3$, —$OCOCH(C_2H_5)C_4H_9$, —$OCOC_6H_5$, —ON=C($CH_3$)$_2$ and —OC($CH_3$)=$CH_2$;
at least any one of -$A^1$, -$A^2$, -$A^3$, —$B^1$ and —$B^2$ in repeat units of —{O—Si(-$A^1$)(-$B^1$)}$_p$— and —{O—Ti(-$A^2$)(-$B^2$)}q and —{O—Al(-$A^3$)}$_r$- (p, q and r are a positive number) is the reactive group, and can be reacted with the hydroxy group on the surface of the respective sheets 10, 20, 30, 40, 50 when they are bonded.

The repeat unit in the compound may be copolymerized via block copolymerization or random copolymerization. The respective sheets 10, 20, 30, 40, 50 are immersed in a solution of polysiloxane having the reactive group which can be reacted with the hydroxy group, and then treated by heating. The polysiloxane having the reactive group is bonded to the hydroxy groups on the surface of the respective sheets 10, 20, 30, 40, 50, and forms the single molecular layer. The reactive groups reacting with the hydroxy groups on the other sheet, which should be bonded, are amplified. The hydroxy groups on the surface of one of the respective sheets 10, 20, 30, 40, 50 are chemically bonded to the polysiloxane having the reactive groups. The hydroxy groups of the respective sheets 10, 20, 30, 40, 50 are indirectly bonded through the polysiloxane having the reactive groups. The respective sheets 10, 20, 30, 40, 50 are finally bonded to each other. Instead of the immersing treatment, a spraying treatment of the solution of polysiloxane having the reactive groups, a dry treatment following it and an optional heating treatment may be conducted.

In order to enhance reactivity to the hydroxy group having bonding ability to an organic group, a tin-containing catalyst and a titanium-containing catalyst may be used. The tin-containing catalyst and the titanium-containing catalyst can enhance a bonding rate, enable a reaction at a low temperature and enhance a condensation reaction generating an ether bond. As the tin-containing catalyst, bis(2-ethylhexanoate)tin, di-n-butylbis(2-ethylhexylmaleate)tin, dibutyltin diacetate and tin dioctyltin dilaurylate are included. As the titanium-containing catalyst, di-butoxide(bis-2,4-pentanedionato)titanium, dipropoxide(bis-2,4-pentanedionato)titanium and titanium-2-ethylhexyloxide are included. These catalysts are used as a mixture of the solution of the polysiloxane having the reactive group.

In the molecular adhesive, as a silane-coupling agent having an alkoxy group without an amino group, an available silane-coupling agent is included. Particularly, a silane-coupling agent having a vinyl group and alkoxy group exemplified by vinyltrimethoxysilane (KBM-1003) and vinyltriethoxysilane (KBE-1003); a silane-coupling agent having an epoxy group and alkoxy group exemplified by 2-(3,4-epoxycyclohexyl)ethyltrimethoxysilane (KBM-303), 3-glycidoxypropyl methyldimethoxysilane (KBM-402), 3-glycidoxypropyl trimethoxysilane (KBM-403), 3-glycidoxypropyl methyldiethoxysilane (KBE-402), and 3-glycidoxypropyl triethoxysilane (KBE-403); a silane-coupling agent having a styryl group and alkoxy group exemplified by p-styryltrimethoxysilane (KBM-1403); a silane-coupling agent having a (meth)acryl group and alkoxy group exemplified by 3-methacryloxypropyl methyldimethoxysilane (KBM-502), 3-methacryloxypropyl methyldiethoxysilane (KBM-503), 3-methacryloxypropyl methyl diethoxysilane (KBE-502), 3-methacryloxypropyl methyldiethoxysilane (KBE-503), 3-acryloxypropyl trimethoxysilane (KBM-5103); a silane-coupling agent having an ureido group and alkoxy group exemplified by 3-ureidopropyltriethoxysilane (KBE-585); a silane-coupling agent having a mercapto group and alkoxy group exemplified by 3-mercaptopropylmethyldimethoxysilane (KBM-802) and 3-mercaptopropyltrimethoxysilane (KBM-803); a silane-coupling agent having a sulfide group and alkoxy group exemplified by bis(triethoxysilylpropyl) tetrasulfide (KBE-846); and a silane-coupling agent having an isocyanate group and alkoxy group exemplified by 3-isocyanatepropyltriethoxysilane (KBE-9007)(all of which is available from Shin-Etsu Chemical Co., Ltd.; trade names) may be exemplified. Further, a silane-coupling agent having a vinyl group and acetoxy group exemplified by vinyltriacetoxysilane (Z-6075); a silane-coupling agent having an allyl group and alkoxy group exemplified by allyltrimethoxysilane (Z-6825); a silane-coupling agent having an alkyl group and alkoxy group exemplified by methyltrimethoxysilane (Z-6366), dimethyldimethoxysilane (Z-6329), trimethylmethoxysilane (Z-6013), methyltriethoxysilane (Z-6383), methyltriphenoxysilane (Z-6721), ethyltrimethoxysilane (Z-6321), n-propyltrimethoxysilane (Z-6265), diisopropyldimethoxysilane (Z-6258), isobutyltrimethoxysilane (Z-2306), diisobutyldimethoxysilane (Z-6275), isobutyltriethoxysilane (Z-6403), n-hexyltrimethoxysilane (Z-6583), n-hexyltriethoxysilane (Z-6586), cyclohexylmethyldimethoxysilane (Z-6187), n-octyltriethoxysilane (Z-6341), and n-decyltrimethoxysilane (Z-6210); a silane-coupling agent having an aryl group and alkoxy group exemplified by phenyltrimethoxysilane (Z-6124); a silane-coupling agent having an alkyl group and chlorosilane group exemplified by n-octyldimethylchlorosilane (ACS-8); a silane-coupling agent of an alkoxysilane exemplified by tetraethoxysilane (Z-6697) (all of which is available from Dow Corning Toray Co., Ltd.; trade names) may be exemplified.

As the silane-coupling agent having the alkoxy group without the amino group, an alkoxysilyl compound having a hydrosilyl group (a SiH group) may be exemplified. For example, $(CH_3O)_3SiCH_2CH_2CH_2Si(CH_3)_2OSi(CH_3)_2H$,
$(C_2H_5O)_3SiCH_2CH_2CH_2Si(CH_3)_2OSi(CH_3)_2H$,
$(CH_3O)_3SiCH_2CH_2CH_2Si(OCH_3)_2OSi(OCH_3)_3$,
$(C_2H_5O)_3SiCH_2CH_2CH_2Si(OCH_3)_2OSi(OCH_3)_3$,
$(C_2H_5O)_3SiCH_2CH_2CH_2Si(CH_3)_2H$,
$(CH_3O)_3SiCH_2CH_2CH_2Si(CH_3)_2H$,
$(i\text{-}C_3H_7O)_3SiCH_2CH_2CH_2Si(CH_3)H_2$,
$(n\text{-}C_3H_7O)_3SiCH_2CH_2CH_2Si(CH_3)_2OSi(CH_3)_2CH_2CH_2Si(CH_3)_2Si(CH_3)_2H$,
$(n\text{-}C_4H_9O)_3SiCH_2CH_2CH_2Si(CH_3)_2OSi(CH_3)_2H$,
$(t\text{-}C_4H_9O)_3SiCH_2CH_2CH_2Si(CH_3)_2OSi(CH_3)_2H$,
$(C_2H_5O)_2CH_3SiCH_2CH_2CH_2Si(CH_3)_2OSi(CH_3)_2H$,
$(CH_3O)_2CH_3SiCH_2CH_2CH_2Si(CH_3)_2OSi(CH_3)_2CH_2CH_2Si(CH_3)_2Si(CH_3)_2H$,
$CH_3O(CH_3)_2SiCH_2CH_2CH_2Si(CH_3)_2OSi(CH_3)_2H$,
$(C_2H_5O)_3SiCH_2CH_2CH_2Si(CH_3)_2OSi(CH_3)_2H$,
$(n\text{-}C_3H_7)_3SiCH_2CH_2CH_2Si(CH_3)_2OSi(CH_3)_2H$,
$(i\text{-}C_3H_7O)_3SiCH_2CH_2CH_2Si(CH_3)_2OSi(CH_3)_2H$,
$(n\text{-}C_4H_9)_3SiCH_2CH_2CH_2Si(CH_3)_2OSi(CH_3)_2H$,
$(t\text{-}C_4H_9)_3SiCH_2CH_2CH_2Si(CH_3)_2OSi(CH_3)_2H$,
$(C_2H_5O)_3SiCH_2CH_2Si(CH_3)_2OSi(CH_3)_2H$,
$(C_2H_5O)_3SiCH_2CH_2CH_2CH_2Si(CH_3)_2OSi(CH_3)_2H$,
$(C_2H_5O)_3SiCH_2CH_2CH_2CH_2CH_2CH_2Si(CH_3)OSi(CH_3)_2H$,
$(C_2H_5O)_3SiCH_2CH_2CH_2CH_2CH_2CH_2CH_2CH_2CH_2CH_2Si(CH_3)_2OSi(CH_3)_2H$,
$(CH_3O)_3SiCH_2C_6H_4CH_2CH_2Si(CH_3)C_6H_4Si(CH_3)_2H$,
$(CH_3O)_2CH_3SiCH_2C_6H_4CH_2CH_2Si(CH_3)_2C_6H_4Si(CH_3)_2H$,
$CH_3O(CH_3)SiCH_2C_6H_4CH_2CH_2Si(CH_3)C_6H_4Si(CH_3)_2H$,
$(C_2H_5O)_3SiCH_2C_6H_4CH_2CH_2Si(CH_3)_2C_6H_4Si(CH_3)_2H$,
$(C_2H_5O)_3SiCH_2CH_2CH_2Si(CH_3)_2C_6H_4OC_6H_4Si(CH_3)_2H$,
$(C_2H_5O)_3SiCH_2CH_2CH_2Si(CH_3)C_2H_4Si(CH_3)_2H$,
$(C_2H_5O)_3SiCH_2CH_2CH_2Si(CH_3)_2O[Si(CH_3)O]_{p1}Si(CH_3)_2H$,
$C_2H_5O(CH_3)SiCH_2CH_2CH_2Si(CH_3)_2O[Si(CH_3)_2O]_{p2}Si(C_2H_5)_2H$,
$(C_2H_5O)_2CH_3SiCH_2CH_2CH_2Si(CH_3)_2O[Si(CH_3)_2O]_{p3}Si(CH_3)_2H$,
$(CH_3)_3SiOSiH(CH_3)O[SiH(CH_3)O]_{p4}Si(CH_3)_3$,
$(CH_3)_3SiO[(C_2H_5OSi(CH_3)CH_2CH_2CH_2)SiCH_3]O[SiH(CH_3)O]_{p5}Si(CH_3)_3$,
$(CH_3)_3SiO[(C_2H_5OSiOCH_3CH_2CH_2CH_2)SiCH_3]O[SiH(CH_3)O]_{p6}Si(CH_3)_3$,
$(CH_3)_3SiO[(C_2H_5OSi(CH_3)CH_2CH_2CH_2)SiCH_3]O[SiH(CH_3)O]_{p7}Si(CH_3)_3$,
$(CH_3)_3SiO[(Si(OC_2H_5)CH_2CH_2CH_2)SiCH_3]O[SiH(CH_3)O]_{p8}Si(CH_3)_3$,
$(CH_3)_3SiOSi(OC_2H_5)_2O[SiH(CH_3)O]_{p9}[Si(CH_3)_2O]_{q1}Si(CH_3)_3$,
$(CH_3)_3SiO[(C_2H_5OSi(CH_3)CH_2CH_2CH_2CH_2CH_2CH_2)Si(CH_3)O][SiH(CH_3)O]_{p10}[Si(C H_3)_2O]_{q2}Si(CH_3)_3$,
$(CH_3)_3SiO[(Si(OCH_3)_3CH_2CH_2CH_2CH_2CH_2CH_2)Si(CH_3)O][SiH(CH_3)O]_{p11}[Si(CH_3)_2 O]_{q3}Si(CH_3)_3$,
$(CH_3)_3SiOSi(OC_2H_5)_2O[SH(C_2H_5)O]_{p12}Si(CH_3)_3$,
$(CH_3)_3SiO[Si(OC_2H_5)_2CH_2CH_2CH_2CH_2CH_2CH_2)Si(C_2H_5)]O[SiH(C_2H_5)O]_{p13}Si(CH_3)_3$,
$(CH_3)_3SiO[(C_2H_5OSi(CH_3)CH_2CH_2CH_2CH_2CH_2CH_2)Si(C_2H_5)]O[SiH(C_2H_5)O]_{p14}Si(C H_3)_3$,
$C_2H_5OSi(CH_3)_2CH_2CH_2CH_2CH_2CH_2CH_2(CH_3)_2SiO[HSi(CH_3)_2OSiC_6H_5O]_{p15}Si(CH_3)_2 H$,
$Si(OCH_3)_3CH_2CH_2CH_2CH_2CH_2CH_2(CH_3)_2SiO[HSi(CH_3)_2OSiC_6H_5O]_{p16}Si(CH_3)_2H$,
$H(CH_3)_2SiO[(C_2H_5OSi(CH_3)_2CH_2CH_2CH_2)Si(CH_3)O][HSiCH_3O]_{p17}Si(CH_3)_2H$,
$H(CH_3)_2SiO[(C_2H_5OSi(CH_3)_2CH_2CH_2CH_2CH_2)Si(CH_3)O][HSiCH_3O]_{p18}Si(CH_3)_2H$,
$H(CH_3)_2SiO[(C_2H_5OSi(CH_3)_2CH_2CH_2CH_2CH_2CH_2CH_2)Si(CH_3)O][HSiCH_3O]_{p19}Si(C H_3)_2H$,
$H(CH_3)_2SiO[(C_2H_5OSi(CH_3)_2CH_2CH_2CH_2CH_2CH_2CH_2CH_2CH_2)Si(CH_3)O][HSiCH_3O]_{p20}Si(CH_3)_2H$,
$H(CH_3)_2SiO[(C_2H_5OSi(CH_3)_2CH_2CH_2CH_2CH_2CH_2CH_2CH_2CH_2CH_2)Si(CH_3)O][HSiCH_3O]_{p21}Si(CH_3)_2H$,
$H(CH_3)_2SiO[(Si(OCH_3)_3CH_2CH_2C_6H_4CH_2CH_2)Si(CH_3)O][HSiCH_3O]_{p22}Si(CH_3)_2H$,
$H(CH_3)_2SiO[(Si(OCH_3)_3CH_2C_6H_4CH_2CH_2CH_2)Si(CH_3)O][HSiCH_3O]_{p23}Si(CH_3)_2H$,
$H(CH_3)_2SiO[(Si(OCH_3)_3CH_2C_6H_4CH_2CH_2)Si(CH_3)O][HSiCH_3O]_{p24}Si(CH_3)_2H$,
$H(CH_3)_2SiO[(Si(OCH_3)_3C_6H_4CH_2CH_2)Si(CH_3)O][HSiCH_3O]_{p25}Si(CH_3)_2H$,
$H(CH_3)_2SiO[(Si(OCH_3)_3CH_2CH_2CH_2)Si(CH_3)O][HSiCH_3O]_{p26}Si(CH_3)_2H$,
$H(CH_3)_2SiO[(Si(OCH_3)_3CH_2CH_2CH_2CH_2)Si(CH_3)O][HSiCH_3O]_{p27}Si(CH_3)_2H$,
$H(CH_3)_2SiO[(Si(OCH_3)_3CH_2CH_2CH_2CH_2CH_2CH_2)Si(CH_3)O][HSiCH_3O]_{p28}Si(CH_3)_2H$,
$H(CH_3)_2SiO[(Si(OCH_3)_3CH_2CH_2CH_2CH_2CH_2CH_2CH_2)Si(CH_3)O][HSiCH_3O]_{p29}Si(CH_3)_2H$,
$H(CH_3)_2SiO[(Si(OCH_3)_3CH_2CH_2CH_2CH_2CH_2CH_2CH_2CH_2)Si(CH_3)O][HSiC H_3O]_{p30}Si(CH_3)_2H$,
$H(CH_3)_2SiO[(Si(OCH_3)_3CH_2CH_2C_6H_4CH_2CH_2)Si(CH_3)O][HSiCH_3O]_{p31}Si(CH_3)_2H$,
$H(CH_3)_2SiO[(Si(OCH_3)_3CH_2C_6H_4CH_2CH_2)Si(CH_3)O][HSiCH_3O]_{p32}Si(CH_3)_2H$, $H(CH_3)_2SiO[(Si(OCH_3)_3CH_2C_6H_4CH_2CH_2)Si(CH_3)O]$
$[HSiCH_3O]_{p33}Si(CH_3)_2H,$
$H(CH_3)_2SiO[(Si(OCH_3)_3C_6H_4CH_2CH_2)Si(CH_3)O]$
$[HSiCH_3O]_{p34}Si(CH_3)_2H,$
$H(CH_3)_2SiO[(Si(OCH_3)_3CH_2CH_2C_6H_4CH_2CH_2)Si(CH_3)$
$O][HSiCH_3O]_{p35}Si(CH_3)_2H,$
$H(CH_3)_2SiO[(CH_3O)Si(CH_3)CH_2CH_2CH_2CH_2CH_2CH_2Si$
$(CH_3)_2OSiC_6H_5O]_{p36}[HSi(CH_3)_2OSiC_6H_5O]_{q4}Si(CH_3)_2H,$
$H(CH_3)_2SiO[Si(OCH_3)_2CH_2CH_2CH_2CH_2CH_2CH_2$
$Si(CH_3)_2OSiC_6H_5O]_{p37}[HSi(CH_3)_2O \quad SiC_6H_5O]_{q5}$
$Si(CH_3)_2H,$
$C_2H_5O(CH_3)_2SiO[SiH(CH_3)O]_{p38}[SiCH_3(C_6H_5)O]_{q6}Si$
$(CH_3)_2H,$
$Si(OC_2H_5)_3CH_2CH_2CH_2CH_2CH_2CH_2(CH_3)_2SiO[SiH$
$(CH_3)O]_{p39}[SiCH_3(C_6H_5)O]_{q7}Si(C H_3)_2H,$
$C_2H_5OSi(CH_3)_2CH_2CH_2CH_2CH_2CH_2CH_2(CH_3)_2SiO[SiH$
$(CH_3)O]_{p40}[SiCH_3(C_6H_5)O]_{q8} Si(CH_3)_2H,$
$H(CH_3)_2SiO(C_2H_5O)Si(CH_3)O[SiH(CH_3)O]_{p41}$ $[SiCH_3$
$(C_6H_5)O]_{q9}Si(CH_3)_2H$ and
$H(CH_3)_2SiO[Si(OC_2H_5)_2CH_2CH_2CH_2Si(CH_3)]O[SiH$
$(CH_3)O]_{p42}[SiCH_3(C_6H_5)O]_{q10}Si(CH_3)_2H$
are optionally used. In these groups, p1 to p42 and q1 to q10 are number of 1 to 100. The alkoxysilyl compound having the hydrosilyl group preferably has the hydrosilyl group of 1 to 99 in a monomolecular thereof.

As the silane-coupling agent having the alkoxy group without the amino group, an alkoxysilyl compound having a hydrosilyl group can be exemplified. For example,
$(C_2H_5O)_3SiCH_2CH=CH_2,$
$(CH_3O)_3SiCH_2CH_2CH=CH_2,$
$(C_2H_5O)_3SiCH_2CH_2CH=CH_2,$
$(CH_3O)_3SiCH_2CH_2CH_2CH_2CH=CH_2,$
$(C_2H_5O)_3SiCH_2CH_2CH_2CH_2CH=CH_2,$
$(C_2H_5O)_3SiCH_2CH_2CH_2CH_2CH_2CH_2CH=CH_2,$
$(CH_3O)_3SiCH_2(CH_2)_7CH=CH_2,$
$(C_2H_5O)_2Si(CH=CH_2)OSi(OC_2H_5)CH=CH_2,$
$(CH_3O)_3SiCH_2CH_2C_6H_4CH=CH_2,$
$(CH_3O)_2Si(CH=CH_2)O[SiOCH_3(CH=CH_2)O]_{t1}Si$
$(OCH_3)_2CH=CH_2,$
$(C_2H_{50}O)_2Si(CH=CH_2)O[SiOC_2H_5(CH=CH_2)O]_{t2}Si$
$(OC_2H_5)_3,$
$(C_2H_5O)_3SiCH_2CH_2CH_2Si(CH_3)_2OSi(CH_3)_2CH_2CH_2[Si$
$(CH_3)_2O]_{t3}CH=CH_2,$
$(CH_3O)_3SiCH_2CH_2CH_2Si(CH_3)_2OSi(CH_3)_2CH_2CH_2[Si$
$(CH_3)_2O]_{t4}CH=CH_2,$
$CH_3O(CH_3)_2SiCH_2CH_2CH_2Si(CH_3)_2OSi(CH_3)_2CH_2CH_2$
$[Si(CH_3)_2O]_{t5}CH=CH_2,$
$(C_2H_5O)_2CH_3SiCH_2CH_2CH_2Si(CH_3)_2OSi(CH_3)_2CH_2CH_2$
$[Si(CH_3)_2O]_{t6}CH=CH_2,$
$(C_2H_5O)_3SiCH_2CH_2CH_2Si(CH_3)_2OSi(CH_3)_2CH_2CH_2[Si$
$(CH_3)_2O]_{t7}CH=CH_2,$
$(C_2H_5O)_3SiCH_2CH_2CH_2Si(CH_3)_2OSi(CH_3)_2CH_2CH_2(Si$
$(CH_3)_3O)Si(CH_3)O[SiCH_3(-)O]_{u1}Si(CH_3)_3CH=CH_2,$
$(C_2H_5O)_3SiCH_2CH_2CH_2Si(CH_3)_2OSi(CH_3)_2CH_2CH_2(Si$
$(CH_3)_3O)Si(CH_3)O[SiCH_3(-)O]_{u2}[Si(CH_3)_2O]_{t8}$
$Si(CH_3)_3CH=CH_2,$
$(C_2H_5O)_2Si(CH=CH_2)O[SiCH_3(OC_2H_5)O]_{u3}$
$Si(OC_2H_5)_2CH=CH_2,$
$(C_2H_5O)_2Si(CH=CH_2)O[Si(OC_2H_5)_2O]_{u4}Si(OC_2H)_2$
$CH=CH_2$ and
$(C_2H_5O)_2Si(CH=CH_2)O[Si(OC_2H_5)_2O]_{u5}Si(OC_2H_5)_2$
$CH=CH_2$
are optionally used. In these groups, t1 to t8 and u1 to u5 are number of 1 to 30. The alkoxysilyl compound having the hydrosilyl group has preferably the vinyl group of 1 to 30 in the monomolecular thereof.

The reaction of these vinyl groups and SiH groups may be enhanced by the metal catalyst, e.g. a compound including platinum for bonding thereof.

As the silane-coupling agent having the alkoxy group without the amino group, an alkoxysilyl compound having the alkoxysilyl group at both terminals may be exemplified. For example,
$(C_2H_5O)_3SiCH_2CH_2Si(OC_2H_5)_3,$
$(C_2H_5O)_2CH_3SiCH_2CH_2Si(OC_2H_5)_3,$
$(C_2H_5O)_3SiCH=CHSi(OC_2H_5)_3,$
$(CH_3O)_3SiCH_2CH_2Si(OCH_3)_3(CH_3O)_3$
$SiCH_2CH_2C_6H_4CH_2CH_2Si(OCH_3)_3,$
$(CH_3O)_3Si[CH_2CH_2]_3Si(OCH_3)_3,$
$(CH_3O)_3Si[CH_2CH_2]_4Si(OCH_3)_3,$
$(C_2H_5O)_2Si(OC_2H_5)_2,$
$(CH_3O)_2CH_3SiCH_2CH_2Si(OCH_3)_2CH_3,$
$(C_2H_5O)_2CH_3SiOSi(OC_2H_5)_2CH_3,$
$(CH_3O)_3SiO[Si(OCH_3)_2O]_{v1}Si(OCH_3)_3,$
$(C_2H_5)_3SiO[Si(OC_2H_5)_2O]_{v2}Si(OC_2H_5)_3$ and
$(C_3H_7)_3SiO[Si(OC_3H_7)_2O]_{v3}Si(OC_3H_7)_3$
In these groups, v1 to v3 are number of 0 to 30.

As the silane-coupling agent having the alkoxy group without the amino group, an alkoxysilyl compound having a hydrolytic group-containing silyl group can be exemplified. For example, an easily-hydrolytic organosilane is optionally used. Particularly, $CH_3Si(OCOCH_3)_3$, $(CH_3)_2Si(OCOCH_3)_2$, $n-C_3H_7Si(OCOCH_3)_3$, $CH_2=CHCH_2Si(OCOCH_3)_3$, $C_6H_5Si(OCOCH_3)_3$, $CF_3CF_2CH_2CH_2Si(OCOCH_3)_3$, $CH_2=CHCH_2Si(OCOCH_3)_3$, $CH_3OSi(OCOCH_3)_3$, $C_2H_5OSi(OCOCH_3)_3$, $CH_3Si(OCOC_3H_7)_3$, $CH_3Si[OC(CH_3)=CH_2]_3$, $(CH_3)_2Si[OC(CH_3)=CH_2]_3$, $n-C_3H_7Si[OC(CH_3)=CH_2]_3$, $CH_2=CHCH_2Si[OC(CH_3)=CH_2]_3$, $C_6H_5Si[OC(CH_3)=CH_2]_3$, $CF_3CF_2CH_2CH_2Si[OC(CH_3)=CH_2]_3$, $CH_2=CHCH_2Si[OC(CH_3)=CH_2]_3$, $CH_3OSi[OC(CH_3)=CH_2]_3$, $C_2H_5OSi[OC(CH_3)=CH_2]_3$, $CH_3Si[ON=C(CH_3)C_2H_5]_3$, $(CH_3)_2Si[ON=C(CH_3)C_2H_5]_2$, $n-C_3H_7Si[ON=C(CH_3)C_2H_5]_3$, $CH_2=CHCH_2Si[ON=C(CH_3)C_2H_5]_3$, $C_6H_5Si[ON=C(CH_3)C_2H_5]_3$, $CF_3CF_2CH_2CH_2Si[ON=C(CH_3)C_2H_5]_3$, $CH_2=CHCH_2Si[ON=C(CH_3)C_2H_5]_3$, $CH_3OSi[ON=C(CH_3)C_2H_5]_3$, $C_2H_5OSi[ON=C(CH_3)C_2H_5]_3$, $CH_3Si[ON=C(CH_3)C_2H_5]_3$, $CH_3Si[N(CH_3)]_3$, $(CH_3)_2Si[N(CH_3)]_2$, $n-C_3H_7Si[N(CH_3)]_3$, $CH_2=CHCH_2Si[N(CH_3)]_3$, $C_6H_5Si[N(CH_3)]_3$, $CF_3CF_2CH_2CH_2Si[N(CH_3)]_3$, $CH_2=CHCH_2Si[N(CH_3)]_3$, $CH_3OSi[N(CH_3)]_3$, $C_2H_5OSi[N(CH_3)]_3$ and $CH_3Si[N(CH_3)]_3$ are included.

As the silane-coupling agent containing the amino group and having the alkoxy group, an available silane-coupling agent is included. Particularly, an alkoxysilyl compound containing the amino group exemplified by N-2-(aminoethyl)-3-aminopropylmethyldimethoxysilane (KBM-602), N-2-(aminoethyl)-3-aminopropyltrimethoxysilane (KBM-603), N-2-(aminoethyl)-3-aminopropyltriethoxysilane (KBE-603), 3-aminopropyltrimethoxysilane (KBM-903), 3-aminopropyltriethoxysilane (KBE-903), 3-triethoxysilyl-N-(1,3-dimethyl-butylidene) propylamine (KBE-9103), N-phenyl-3-aminopropyltrimethoxysilane (KBM-573) and N-(vinylbenzyl)-2-aminoethyl-3-aminopropyltrimethoxysilane hydrochloride (KBM-575) (all of which is available from Shin-Etsu Chemical Co., Ltd.; trade names) may be used. Further, an alkoxysilyl compound containing an amino group exemplified by 3-aminopropyltrimethoxysilane (Z-6610), 3-aminopropyltrimethoxysilane (Z-6611), 3-(2-aminoethyl)aminopropyltrimethoxysilane (Z-6094), 3-phenylaminopropyltrimethoxysilane (Z-6883), and N[3-(trimethoxysilyl)propyl]-N'-[(ethenylphenyl)methyl]-1,2- ethanediamine hydrochloride (Z-6032)(all of which is available from Dow Corning Toray Co., Ltd.; trade names) may be used.

When the base sheet 10 and the covering sheet 50 are made from the cycloolefin resin and the thin sheet 20, the thick sheet 40 and the partition sheet 30 are made from the silicone rubber, they are preferably bonded by using the molecular adhesive such as the silane-coupling agent. Specifically, the respective sheets 10, 20, 30, 40, 50 immerse in the molecular adhesive of 0.05 to 1% by weight of an alcohol solution such as the methanol solution, and is dried, followed by being bonded. When the concentration of the molecular adhesive is excessively high, the respective sheets 10, 20, 30, 40, 50 are removed at the bonding surfaces thereof each other. When the concentration thereof is excessively low, the respective sheets 10, 20, 30, 40, 50 cannot be sufficiently bonded.

The respective sheets 10, 20, 30, 40, 50 are stacked each other, bonded by the directive covalent bond and/or the indirective covalent bond through the molecular adhesive, and integrated. When the respective sheets 10, 20, 30, 40, 50 are bonded, a treatment of any one of a dry type treatment such as the corona discharge treatment and a molecular adhesive treatment is preferably conducted to a face any one of the sheets 10, 20, 30, 40, 50 which should be bonded. Only one of the dry type treatment and the molecular adhesive treatment may be conducted. These treatments may be continuously and alternately conducted. For example, the sheets 10, 20, 30, 40, 50 may be bonded by only the dry type treatment, by the molecular adhesive treatment following the dry type treatment, by the molecular adhesive treatment following the dry type treatment and the additional dry type treatment, by only the molecular adhesive treatment, by the dry type treatment following the molecular adhesive treatment, or by the dry type treatment following the molecular adhesive treatment and the additional molecular treatment.

The respective sheets 10, 20, 30, 40, 50 may be treated by the corona treatment for the face thereof which should be bonded, stacked under the atmospheric pressure and then may be bonded by the covalent bond which is formed under the atmospheric pressure. Alternatively, they may be bonded by the covalent bond which is formed under a reduced pressure condition or a pressurized condition. Approaching of the active groups such as OH or the reactive functional group of the silane-coupling agent which reacts therewith is enhanced by removing gaseous media of contact boundaries under the reduced pressure condition or a vacuum condition. As the reduced pressure condition or the vacuum condition, for example, 50 torr or less, more particularly, the reduced pressure conditions of 50 to 10 torr or the vacuum conditions of less than 10 torr, more particularly, less than 10 to $1\times10^{-3}$ torr, preferably less than 10 to $1\times10^{-2}$ torr. Alternatively, the approaching thereof may be enhanced by adding a stress (a load) of e.g. 10 to 200 kgf to the contact boundaries thereof, and further by heating the contact boundaries thereof.

The corona discharge treatment for the face of the respective sheets 10, 20, 30, 40, 50 is conducted under the conditions of e.g. power source: AC 100V, output voltage: 0 to 20 kV, oscillating frequency: 0 to 40 kHz for 0.1 to 60 seconds, and temperature: 0 to 60° C. by using an apparatus for an atmospheric pressure corona surface modification (e.g. trade name of CoronaMaster supplied by Shinko Electric & Instrumentation Co., Ltd.). The corona discharge treatment may be conducted to the face wetted with water, alcohols, acetones or esters etc.

The treatment which is conducted in order to activate the surface of the respective sheets 10, 20, 30, 40, 50 may be an atmospheric pressure plasma treatment and/or an ultraviolet irradiation treatment (a well-known UV treatment which generates ozone by an UV irradiation treatment and an excimer treatment).

The atmospheric pressure plasma treatment is conducted under conditions of e.g. plasma processing speed: 10 to 100 mm/s, power source: 200 or 220V AC (30 A), compressed air: 0.5 MPa (1 NL/min.), and 10 kHz/300 W to 5 GHz, electric power: 100 to 400 W, and irradiation period of time: 0.1 to 60 seconds by using an air plasma generator (trade name of Aiplasma supplied by Panasonic Corporation).

The ultraviolet irradiation treatment is conducted under conditions of e.g. 50 to 1500 $mJ/cm^2$ of the cumulative amount of light by using an excimer rump optical source (trade name of L11751-01 supplied by Hamamatsu Photonics K.K.).

Material of the partition sheet 30 is preferably elastomer, more preferably silicone rubber and even more preferably the three-dimensional silicone rubber. As the silicone rubber, vinylmethyl silicone rubber (VMQ), methylphenyl silicone rubber (PVMQ), fluoromethyl silicone rubber (FVMQ) and dimethyl silicone rubber (MQ) are included. As the three-dimensional silicone rubber, the silicone rubber exemplified by peroxide crosslinking type silicone rubber, addition crosslinking type silicone rubber, ultraviolet crosslinking type silicone rubber and condensation crosslinking type silicone rubber, and a three-dimensional silicone rubber elastomer having a sterical crosslinking structure are mainly included. The three-dimensional silicone rubber elastomer is produced by crosslinking a blended product of the silicone rubber and olefin rubber in a mold etc.

The peroxide crosslinking type silicone rubber which is a raw material of the three-dimensional silicone rubber elastomer is not specifically limited as far as the rubber synthesized from a silicone raw compound which is crosslinked by a peroxide type crosslinking agent. Particularly, polydimethylsiloxane (molecular weight 500,000 to 900,000), vinylmethylsiloxane/polydimethylsiloxane copolymer (molecular weight: 500,000 to 900,000), vinyl-terminated polydimethylsiloxane (molecular weight: 10,000 to 200,000), vinyl-terminated diphenylsiloxane/polydimethylsiloxane copolymer (molecular weight: 10,000 to 100,000), vinyl-terminated diethyl siloxane/polydimethyl siloxane copolymer (molecular weight: 10,000 to 50,000), vinyl-terminated trifluoropropylmethylsiloxane/polydimethylsiloxane copolymer (molecular weight: 10,000 to 100,000), vinyl-terminated polyphenylmethylsiloxane (molecular weight: 1,000 to 10,000), vinylmethylsiloxane/dimethylsiloxane copolymer, trimethylsiloxane group-terminated dimethylsiloxane/vinylmethylsiloxane copolymer, trimethylsiloxane group-terminated dimethylsiloxane/vinylmethylsiloxane/diphenylsiloxane copolymer, trimethylsiloxane group-terminated dimethylsiloxane/vinylmethylsiloxane/ditrifluoropropylmethylsiloxane copolymer, trimethylsiloxane group-terminated polyvinylmethyl syloxane, methacryloxypropyl group-terminated polydimethylsiloxane, acryloxypropyl group-terminated polydimethylsiloxane, (methacryloxypropyl)methyl siloxane/dimethyl siloxane copolymer and (acryloxypropyl)methyl siloxane/dimethyl siloxane copolymer may be exemplified.

The addition type silicone rubber which is a raw material of the three-dimensional silicone rubber elastomer can be obtained by synthesis in the presence of Pt containing catalyst using below composition. The composition comprises vinyl group-containing polysiloxanes and H group-containing polysiloxanes. As vinyl group-containing polysiloxanes, vinylmethylsiloxane/polydimethylsiloxane copolymer (molecular weight: 500,000 to 900,000), vinyl-terminated polydimethylsiloxane (molecular weight: 10,000 to 200,000), vinyl-terminated diphenylsiloxane/polydimethylsiloxane copolymer (molecular weight: 10,000 to 100,000), vinyl-terminated diethyl siloxane/polydimethyl siloxane copolymer (molecular weight: 10,000 to 50,000), vinyl-terminated trifluoropropylmethylsiloxane/polydimethylsiloxane copolymer (molecular weight: 10,000 to 100,000), vinyl-terminated polyphenylmethylsiloxane (molecular weight: 1,000 to 10,000), vinylmethylsiloxane/dimethylsiloxane copolymer, trimethylsiloxane group-terminated dimethylsiloxane/vinylmethylsiloxane/diphenylsiloxane copolymer, trimethylsiloxane group-terminated dimethylsiloxane/vinylmethylsiloxane/ditrifluoropropylmethylsiloxane copolymer and trimethylsiloxane group-terminated polyvinylmethylsiloxane etc. are included. As H group-containing polysiloxanes, H-terminated polysiloxane (molecular weight: 500 to 100,000), methyl H siloxane/dimethylsiloxane copolymer, polymethyl H siloxane, polyethyl H siloxane, H-terminated polyphenyl(dimethyl H siloxy)siloxane, methyl H siloxane/phenylmethyl siloxane copolymer and methyl H siloxane/octylmethylsiloxane copolymer etc. are included.

The other composition may comprise amino group-containing polysiloxanes, epoxy group-containing polysiloxanes, acid anhydride group-containing polysiloxanes or isocyanato group-containing compounds. As amino group-containing polysiloxanes, aminopropyl-terminated polydimethylsiloxane, aminopropylmethylsiloxane/dimethylsiloxane copolymer, aminoethylaminoi sobutylmethyl siloxane/dimethyl siloxane copolymer, aminoethylaminopropylmethoxysiloxane/dimethyl siloxane copolymer, and dimethylamino-terminated polydimethylsiloxane are included. As epoxy group-containing polysiloxanes, epoxypropyl-terminated polydimethylsiloxane, and (epoxycyclohexylethyl)methylsiloxane/dimethylsiloxane copolymer etc. are included. As acid anhydride group-containing polysiloxanes, succinic acid anhydride-terminated polydimethylsiloxane is included. As the isocyanato group-containing compounds, toluyldiisocyanate, 1,6-hexamethylene diisocyanate and the like are included.

The condensation type silicone rubber of material for the three-dimensional silicone rubber elastomer can be obtained by synthesis using below composition. The composition comprises a composition of a homocondensation component consisting of silanol group-terminated polysiloxanes synthesized in the presence of tin containing catalyst, a composition containing their silanol group-terminated polysiloxanes and a crosslinking agent, a composition containing their silanol group-terminated polysiloxanes and a composition of terminal-blocked polysiloxanes such as terminal-polysiloxane.

As silanol group-terminated polysiloxanes, silanol-terminated polydimethyl siloxane (molecular weight: 500 to 200,000), silanol-terminated polydiphenylsiloxane, silanol-terminated polytrifluoromethyl siloxan and silanol-terminated diphenyl siloxane/dimethylsiloxane copolymer etc. are included.

As the crosslinking agent, tetraacetoxysilane, triacetoxymethylsilane, di t-butoxydiacetoxysilane, vinyltriacetoxysilane, tetraethoxysilane, triethoxymethylsilane, bis (triethoxysilyl)ethane, tetra-n-propoxysilane, vinyltrimethoxysilane, methyltris(methylethylketoxim)silane, vinyltris(methylethylketoximino)silane, vinyltriisopropenoxysilane, triacetoxymethylsilane, tri(ethylmethyl) oximmethylsilane, bis(N-methylb enzoamido)ethoxymethyl silane, tris(cyclohexylamino)methylsilane, triacetoamidomethylsilane and tridimethylamino methylsilane are included.

As terminal-blocked polysiloxanes, chloro-terminated polydimethylsilioxane and diacetoxymethyl-terminated polydimethylsiloxane are included.

The blended product which is a raw material of the three-dimensional silicone rubber elastomer contains the silicone rubber and the olefin rubber. As the olefin rubber used for the blended product, 1, 4-cis-butadiene rubber, isoprene rubber, styrene-butadiene copolymer rubber, polybutene rubber, polyisobutylene rubber, ethylene-propylene rubber, ethylene-propylene-diene rubber, chlorinated ethylene-propylene rubber and chlorinated butyl rubber are included.

As the elastomer except for the silicone rubber, butyl rubber, ethylene-propylene rubber, ethylene-propylene-diene rubber, urethane rubber, fluoro-rubber, acryl rubber, butadiene rubber, styrene-butadiene rubber, acrylonitrile-butadiene rubber, chloroprene rubber, isoprene rubber, natural rubber, 1, 2-polybutadiene, styrene type thermoplastic elastomer, olefin type thermoplastic elastomer, polyester type thermoplastic elastomer and urethane thermoplastic elastomer are included. These rubbers may be used solely or mixture thereof.

As the material of the base sheet 10 and the covering sheet 50, the cycloolefin resin is mentioned above. Further, the material may be used in the same material as the partition sheet 30. As the other resins for the base sheet 10 and the covering sheet, for example, polycarbonate resin, acryl resin, epoxy resin, polyethylene terephthalate resin, polybutylene terephthalate resin, cellulose and derivatives thereof, hydroxyethyl cellulose, starch, diacetylcellulose, surface-saponified vinylacetate resin, low-density polyethylene, high-density polyethylene, i-polypropylene, petroleum resin, polystyrene, s-polystyrene, coumarone-indene resin, terpene resin, styrene-divinylbenzene copolymer, ABS resin, polymethyl acrylate, polyethyl acrylate, polyacrylonitrile, polymethyl methacrylate, polyethyl methacrylate, polycyanoacrylate, polyvinyl acetate, polyvinyl alcohol, polyvinylformal, polyvinylacetal, polyvinyl chloride, vinyl chloride-vinyl acetate copolymer, vinyl chloride-ethylene copolymer, polyvinylidene fluoride, vinylidene fluoride-ethylene copolymer, vinylidene fluoride-propylene copolymer, 1,4-trans-polybutadiene, polyoxymethylene, polyethylene glycol, polypropylene glycol, phenol-formalin resin, cresol-formalin resin, resorcin resin, melamine resin, xylene resin, toluene resin, glyptal resin, modified glyptal resin, unsaturated polyester resin, allylester resin, 6-nylon, 6,6-nylon, 6,10-nylon, polyimide, polyamide, polybenzimidazole, polyamideimide, silicon resin, silicone rubber, silicone resin, furan resin, polyurethane resin, polyphenyleneoxide, polydimethylphenyleneoxide, mixture of triallyl isocyanurate compound with polyphenyleneoxide or polydimethylphenyleneoxide, mixture of (polyphenyleneoxide or poly-dimethylphenyleneoxide, triallyl isocyanurate, peroxide), polyxylene, polyphenylenesulfide (PPS), polysulfone (PSF), polyethersulfone (PES), polyether ether ketone (PEEK), polyimide (PPI), polytetrafluroethylene (PTFE), liquid crystal resin, aramid fiber, carbon fiber, polymeric material exemplified by a mixture of a plurality of these resins and crosslinked products thereof can be exemplified.

The material of the thin sheet 20 and the thick sheet 40 may be same as the partition sheet 30, or same as the base sheet 10 and the covering sheet 50. When the thin sheet 20 and the thick sheet 40 are made from the elastomer having the high elasticity such as the partition sheet 30, the respective flow paths 21, 41 are extended by pressure of the liquid specimen. The liquid specimen can be smoothly flowed in the respective flow paths 21, 41. When the thin sheet 20 and the thick sheet 40 are made from the resin similar to the base sheet 10 and the covering sheet 50, it is prevented that vapor of the liquid specimen, which is generated by rising temperature when the PCR reaction, is absorbed from the side face of the reaction cistern 45 in the sheets 20, 40, because differently from the silicone rubber, the resin has no hygroscopicity.

The respective sheets 10, 20, 30, 40, 50 may be contain a platinum catalyst in concentration of 10 to 1000 ppm in the terms of platinum. As the platinum catalyst, for example, a 1,3-divinyl-1,1,3,3-tetramethyldisiloxane platinum (0) complex (Pt (dvs)) 2.1-2.4% xylene solution (available from Gelest Inc.) may be included. According to the platinum catalyst, at least one of the two faces between the respective sheets 10, 20, 30, 40, 50, which should be bonded, may be easily bonded via the covalent bond by the active groups which generate through the corona treatment, the plasma treatment or the ultraviolet treatment (the well-known UV treatment which generates ozone by the UV irradiation treatment and the excimer treatment).

Incidentally, the base sheet 10 and the covering sheet 50 may be made from the same material as the thin sheet 20, the partition sheet 30 and the thick sheet 40.

In the respective sheets 10, 20, 30, 40, 50, at least one of the two faces therebetween, which should be bonded, may contain the silane-coupling agent having 0.5 to 10 parts by mass concentration of a vinylalkoxysilane unit containing a vinylalkoxysilyl group, e.g. polydimethylsiloxane. The respective sheets 10, 20, 30, 40, 50 can be strongly bonded by a covalent bond different from the ether bond which is the covalent bond formed by being bonded the vinyl groups of the silane-coupling agent and the vinyl groups and hydrogen-siloxane groups in the peroxide or the platinum catalyst. In this case, when the platinum catalyst is contained, the covalent bond is easily formed and thus, it is preferable.

EMBODIMENTS

Embodiments of the present invention will be described in detail below, but the scope of the present invention is not restricted to these embodiments.

Example 1

(Preparing a Silicone Rubber Sheet)

Methylvinyl silicone rubber (available from Dow Corning Toray Co., Ltd.; trade name: SH851U) as silicone rubber in an amount of 100 part by mass and 50% silica solution of 2,5-dimethyl-2,5-di(t-butylperoxy)hexane (available from Dow Corning Toray Co., Ltd.; trade name: RC-4) as a peroxy catalyst in an amount of 0.5 part by mass were kneaded, and then a silicone rubber composition was obtained. After the silicone rubber composition was heated and pressurized, silicone rubber sheets having 50, 100 and 400 μm thickness were prepared, respectively.

(Producing Check-Valves Having Various Shapes and Thicknesses of Partition Sheets)

Figure 10:
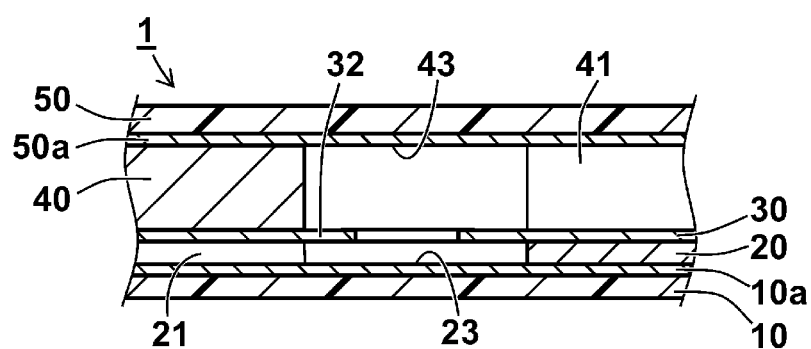
FIG. 10 is a schematic cross-sectional view of the check-valve of Example according to the present invention.

A check-valve 1 of Example 1 was produced as follows. As shown in FIG. 10, the check-valve 1 had a structure in which a water repellent sheet 50a which was made form same material as a water repellent sheet 10a and had a same shape as a covering sheet 50 was bonded to a thin sheet 40 and the covering sheet 50 while being sandwiched therebetween. A shape of the check-valve 1 was shown in FIG. 11(1). A through-pass hole 31 was opened at a central part of both valve chambers 22, 42 having a cylindrical shape. The through-pass hole 31 had an elongated circular shape having vertical longitudinal sides relative to respective flow paths 21, 41. After a cycloolefin resin sheet (available from Zeon Corporation; trade name: ZeonorFilm ZF16-188; 188 μm thickness) was cut out by using a laser processing apparatus (supplied by COMNET Corporation, trade name: LaserPro SPILIT), the base sheet 10 and the covering sheet 50 were prepared. After a silicone rubber sheet having 50 μm thickness was cut out by using the laser processing apparatus, a partition sheet 30 was prepared. In the same manner as this, the water repellent sheets 10a, 50a were prepared by cutting out a silicone rubber sheet having 100 μm thickness, and the thick sheet 40 was prepared by cutting out a silicone rubber sheet having 400 μm thickness.

The water repellent sheets 10a, 50a and the respective sheets 20, 30, 40 were activated by three times of corona discharge treatments in conditions of 1 mm gap length, 13.5 kV voltage and 70 mm/second. The base sheet 10 and the covering sheet 50 were washed with ethanol, and immersed in an ethanol solution containing 2,6-diazido-4-{3-(triethoxysilyl)propylamino}-1,3,5-triazine (P-TES), and then dried by using a blow-gun. The surface of the base sheet 10 and the covering sheet 50 were activated by irradiating UV light (200 mJ/cm$^2$, 254 nm wave length), respectively. The respective sheets 10, 10a, 20, 30, 40, 50a, 50 were aligned while being stacked in this order, laminated, and then bonded by compressing at 70 kgf with heat at 80° C. for 10 minutes. The check-valve 1 having an inner flange 32 of 50 μm thickness, a shallow flow path 21 and a flow-in valve chamber 22 of 100 μm depths, a deep flow path 41 and a flow-out valve chamber 42 of 400 μm depths, and further having the shape(1) was produced. In the check-valve 1, a material of a bottom surface 23 was the water repellent sheet 10a, and a material of an upper surface 43 was the water repellent sheet 50a. Incidentally, the ends of the shallow flow path 21 and the deep flow path 41 were an inlet and an outlet which are connected and opened to external side.

Figure 11:
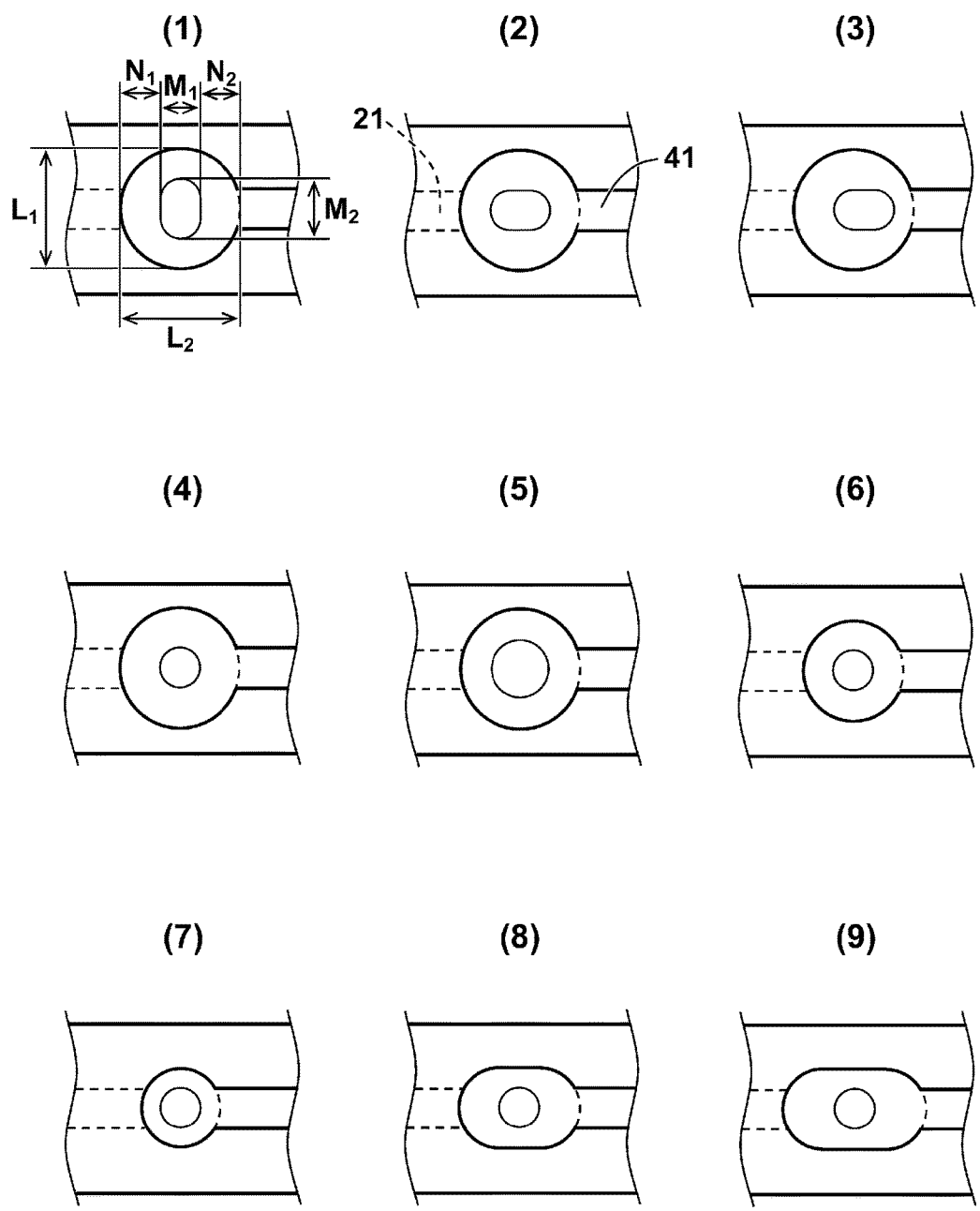
FIG. 11 is a schematic plan view of the check-valve of Example according to the present invention.

In addition, check-valves 1 having shapes(2) to (9) shown in FIG. 11(2) to (9) were produced in the same manner as the check valve 1 having the shape(1) except for altering the shape thereof to the shapes(2) to (9). With regard to dimensions of the valve chambers 22, 42 in FIG. 11, a length of a perpendicular direction relative to the respective flow paths 21, 41 was $L_1$, and a parallel length of a direction relative thereto was $L_2$. With regard to dimensions of the through-pass hole 31, a length of the parallel direction relative to the respective flow paths 21, 41 was $M_1$, and a length of a perpendicular direction relative thereto was $M_2$. With regard to widths of the inner flange 32, and a width of a shallow flow path side inner flange 32a was $N_1$, and a width of a deep flow path side inner flange 32b was $N_2$.

Furthermore, the partition sheet 30 was altered to a silicone rubber sheet having 100 μm thickness, and check-valves 1 of the shapes(1) to (9) having the inner flange 32 of 100 μm thickness were produced. These check-valves 1 were same as the above check-valves 1 except that the thickness of the partition sheet 30 was different.

The respective dimensions of the check-valves 1 having the shapes shown in FIG. 11(1) to (9) were shown in Table 1.

TABLE 1

|  | Dimension of Valve chamber (mm) | | Dimension of Through-pass hole (mm) | | Width of Shallow flow path side inner flange (mm) | Width of Deep flow path side inner flange (mm) |
| --- | --- | --- | --- | --- | --- | --- |
|  | $L_1$ | $L_2$ | $M_1$ | $M_2$ | $N_1$ | $N_2$ |
| Shape (1) | 3.00 | 3.00 | 1.00 | 1.50 | 1.00 | 1.00 |
| Shape (2) | 3.00 | 3.00 | 1.50 | 1.00 | 0.75 | 0.75 |
| Shape (3) | 3.00 | 3.00 | 1.50 | 1.00 | 1.00 | 0.50 |
| Shape (4) | 3.00 | 3.00 | 1.00 | 1.00 | 1.00 | 1.00 |
| Shape (5) | 3.00 | 3.00 | 1.50 | 1.50 | 0.75 | 0.75 |
| Shape (6) | 2.50 | 2.50 | 1.00 | 1.00 | 0.75 | 0.75 |
| Shape (7) | 2.00 | 2.00 | 1.00 | 1.00 | 0.50 | 0.50 |
| Shape (8) | 2.00 | 3.00 | 1.00 | 1.00 | 1.00 | 1.00 |
| Shape (9) | 2.00 | 3.50 | 1.00 | 1.00 | 1.25 | 1.25 |

(Pressuring Evaluation of the Check-Valve)

Air was flowed into the check-vale 1 through the end of the shallow flow path 21, and maximum pressure for which the check-valve 1 which could be maintained an open state was measured. The measured maximum pressure was defined as a normal flow maximum pressure. Air was flowed into the check-valve 1 through the end of the deep flow path 41, and minimum pressure for which the check-valve 1 became a closed state was measured. The measured minimum pressure was defined as a reverse flow minimum pressure. These pressures were measured by using Micro-Flowmate (supplied by Arbiotec Co., Ltd. and AIDA ENGINEERING LTD.). A measured pressure range was from 3 to 200 kPa. The pressures were measured according to the shapes(1) to (9) and the thicknesses of the partition sheet 30. The results are shown in Table 2.

TABLE 2

|  | Normal flow maximum pressure (kPa) | | Reverse flow minimum pressure (kPa) | |
| --- | --- | --- | --- | --- |
|  | Partition sheet thickness | | | |
|  | 50 μm | 100 μm | 50 μm | 100 μm |
| Shape (1) | 30 | 50 | <3 | 10 |
| Shape (2) | 40 | 110 | <3 | <3 |
| Shape (3) | >200 | >200 | <3 | 10 |
| Shape (4) | 30 | 70 | <3 | <3 |
| Shape (5) | >200 | >200 | <3 | 10 |
| Shape (6) | 40 | >200 | <3 | 5 |
| Shape (7) | >200 | >200 | 5 | 30 |
| Shape (8) | >200 | >200 | 5 | 30 |
| Shape (9) | >200 | >200 | 5 | 20 |

According to the check-valves 1 which appropriately set the shapes and the thicknesses of the partition sheet 30, values of the normal flow maximum pressure and the reverse flow minimum pressure could be freely controlled.

(Pumping-Liquid Evaluation of the Check-Valve)

Ion-exchange water was injected into the check-valve 1 through the end of the shallow flow path 21, and maximum flow of the check-valve 1 which could be maintained an open state was measured. The measured maximum flow was defined as a normal flow maximum flow. Ion-exchange water was flowed into the check-valve 1 through the end of the deep flow path 41, and minimum flow for which the check-valve 1 became a closed state was measured. The measured minimum flow was defined as a reverse flow minimum flow. Ion-exchange water was injected by using a syringe pump (supplied by TERUMO CORPORATION, trade name: TERUFUSION (registered trademark) syringe pump TE-331S, a settable range of flow: 0.1 to 150.0 mL/h). The flows were measured according to the shapes(1) to (9) and the thicknesses of the partition sheet 30. The results are shown in Table 3.

TABLE 3

|  | Normal flow maximum flow (mL/h) | | Reverse flow maximum flow (mL/h) | |
| --- | --- | --- | --- | --- |
|  | Partition sheet thickness | | | |
|  | 50 μm | 100 μm | 50 μm | 100 μm |
| Shape (1) | >150 | >150 | <1 | <1 |
| Shape (2) | >150 | >150 | <1 | <1 |
| Shape (3) | >150 | >150 | <1 | 10 |
| Shape (4) | >150 | >150 | <1 | <1 |
| Shape (5) | >150 | >150 | <1 | 10 |
| Shape (6) | >150 | >150 | <1 | 10 |
| Shape (7) | >150 | >150 | <1 | 20 |
| Shape (8) | >150 | >150 | <1 | 10 |
| Shape (9) | >150 | >150 | <1 | 10 |

According to the check-valve 1 which appropriately set the shapes thereof and the thicknesses of the partition sheet 30, values of the normal flow maximum flow and the reverse flow minimum flow could be freely controlled.

Example 2

(Evaluation of Check-Valves in which Shapes Thereof and Thicknesses of Thick Sheets were Altered)

Check-valves 1 of shapes(1) to (9) having a structure shown in FIG. 10 and shapes shown in FIG. 11(1) to (9) were produced in the same manner as Example 1 except that thickness of the thick sheet 40 was altered to two different thicknesses of 200 μm and 300 μm, and the thickness of the partition sheet 30 was only 50 μm. With regard to these produced check-valves 1, the pressuring evaluation and the pumping-liquid evaluation were conducted in the same manner as Example 1. The results of the both evaluations are shown in Table 4.

TABLE 4

|  | Pressuring evaluation | | | | Pumping-liquid evaluation | | | |
| --- | --- | --- | --- | --- | --- | --- | --- | --- |
|  | Normal flow maximum pressure (kPa) | | Reverse flow minimum pressure (kPa) | | Normal flow maximum flow (mL/h) | | Reverse flow maximum flow (mL/h) | |
|  | Thick sheet thickness | | | | | | | |
|  | 200 μm | 300 μm | 200 μm | 300 μm | 200 μm | 300 μm | 200 μm | 300 μm |
| Shape (1) | <3 | 10 | <3 | <3 | 50 | >150 | <1 | <1 |
| Shape (2) | <3 | 10 | <3 | <3 | 50 | >150 | <1 | <1 |
| Shape (3) | 5 | 15 | <3 | <3 | >150 | >150 | <1 | <1 |

TABLE 4-continued

| | Pressuring evaluation | | | | Pumping-liquid evaluation | | | |
|---|---|---|---|---|---|---|---|---|
| | Normal flow maximum pressure (kPa) | | Reverse flow minimum pressure (kPa) | | Normal flow maximum flow (mL/h) | | Reverse flow maximum flow (mL/h) | |
| | Thick sheet thickness | | | | | | | |
| | 200 μm | 300 μm | 200 μm | 300 μm | 200 μm | 300 μm | 200 μm | 300 μm |
| Shape (4) | <3 | 5 | <3 | <3 | 50 | >150 | <1 | <1 |
| Shape (5) | 5 | 10 | <3 | <3 | 100 | >150 | <1 | <1 |
| Shape (6) | 5 | 20 | <3 | <3 | >150 | >150 | <1 | <1 |
| Shape (7) | 15 | 50 | 5 | 5 | >150 | >150 | <1 | <1 |
| Shape (8) | 10 | 25 | 5 | <3 | >150 | >150 | <1 | <1 |
| Shape (9) | 10 | 20 | <3 | <3 | >150 | >150 | <1 | <1 |

According to the check-valve 1 which appropriately set the shapes thereof and the thicknesses of the thick sheet 40, values of the normal flow maximum pressure, the reverse flow minimum pressure, the normal flow maximum flow and the reverse flow minimum flow could be freely controlled.

Example 3

(Evaluation of Check-Valves Having Slit)

Figure 12:
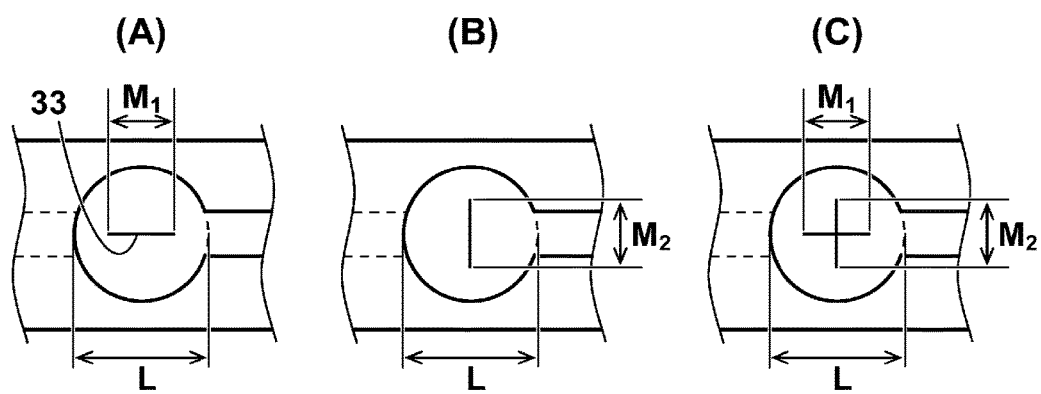
FIG. 12 is a schematic plan view of the check-valve of Example according to the present invention.

Check-valves 1 of shapes (10) to (30) having a slit 33 shown in FIG. 12(A) to (C) were produced in the same manner as Example 1. The dimension L of the valve chamber and dimensions $M_1$, $M_2$ of the slit were altered according to the shapes(10) to (30), respectively. The thickness of the partition sheet 30 was 50 μm. The slit 33 shown in FIG. 12(A) had a parallel straight line shape relative to the both flow paths 21, 41. The slit 33 shown in FIG. 12(B) had a perpendicular straight line shape relative to the both flow paths 21, 41. The slit 33 shown in FIG. 12(C) had a cross shape. All slits 33 were cut into the central part of the inner flange 32. With regard to these check-valves 1, the pressuring evaluation and the pumping-liquid evaluation were conducted in the same manner as Example 1. The respective dimensions L, $M_1$ and $M_2$, and the results of the both evaluations are shown in Table 5. "Slit type" in Table 5 indicates any one of the shapes shown in FIG. 12(A) to (C).

TABLE 5

| | Check-valve | | | | Pressuring evaluation | | Pumping-liquid evaluation | |
|---|---|---|---|---|---|---|---|---|
| | | dimension | | | Normal | Reverse | Normal | Reverse |
| | Slit type | Valve chamber (mm) L | Slit (mm) $M_1$ | Slit (mm) $M_2$ | flow maximum pressure (kPa) | flow minimum pressure (kPa) | flow maximum flow (mL/h) | flow maximum flow (mL/h) |
| Shape (10) | (A) | 3.00 | 1.00 | — | 10 | <3 | >150 | <1 |
| Shape (11) | (B) | 3.00 | — | 1.00 | 10 | <3 | >150 | <1 |
| Shape (12) | (C) | 3.00 | 1.00 | 1.00 | 10 | <3 | >150 | <1 |
| Shape (13) | (A) | 2.50 | 1.00 | — | 20 | <3 | >150 | <1 |
| Shape (14) | (B) | 2.50 | — | 1.00 | 20 | <3 | >150 | <1 |
| Shape (15) | (C) | 2.50 | 1.00 | 1.00 | 20 | <3 | >150 | <1 |
| Shape (16) | (A) | 2.00 | 1.00 | — | 40 | <3 | >150 | <1 |
| Shape (17) | (B) | 2.00 | — | 1.00 | 40 | <3 | >150 | <1 |
| Shape (18) | (C) | 2.00 | 1.00 | 1.00 | >200 | <3 | >150 | <1 |
| Shape (19) | (A) | 3.00 | 0.500 | — | 5 | <3 | >150 | <1 |
| Shape (20) | (B) | 3.00 | — | 0.500 | 5 | <3 | >150 | <1 |
| Shape (21) | (C) | 3.00 | 0.500 | 0.500 | 5 | <3 | >150 | <1 |
| Shape (22) | (A) | 2.50 | 0.500 | — | 10 | <3 | >150 | <1 |
| Shape (23) | (B) | 2.50 | — | 0.500 | 10 | <3 | >150 | <1 |
| Shape (24) | (C) | 2.50 | 0.500 | 0.500 | 10 | <3 | >150 | <1 |
| Shape (25) | (A) | 2.00 | 0.500 | — | 20 | <3 | >150 | <1 |
| Shape (26) | (B) | 2.00 | — | 0.500 | 20 | <3 | >150 | <1 |
| Shape (27) | (C) | 2.00 | 0.500 | 0.500 | 20 | <3 | >150 | <1 |
| Shape (28) | (A) | 1.50 | 0.500 | — | 60 | <3 | >150 | <1 |
| Shape (29) | (B) | 1.50 | — | 0.500 | 60 | <3 | >150 | <1 |
| Shape (30) | (C) | 1.50 | 0.500 | 0.500 | 60 | <3 | >150 | <1 |

According to the check-valve 1 which appropriately set the dimensions of the valve chambers 22, 42, the shapes of the slit 33 and the dimensions thereof, values of the normal flow maximum pressure, the reverse flow minimum pressure, the normal flow maximum flow and the reverse flow minimum flow could be freely controlled.

Example 4

(Evaluation of Check-Valves in which a Contact Angle of a Bottom Surface of the Flow-in Valve Chamber were Altered)

A check-valve A1 having the structure (a material of a sheet for the bottom surface 23 was a silicone rubber) shown in FIG. 10 and the shape shown in FIG. 11(3) was produced in the same manner as Example 1. While a producing process of the check-valve A1, the silicone rubber sheet was allowed to stand for 30 hours after an activation treatment thereof, and then ion-exchange water was injected into the check-valve A1 so as to be a reverse flow. The reverse flow minimum flow was measured. The activation treatment in the same manner as the producing process of the check-valve A1 was conducted to a sample for measuring the contact angle made of the silicone rubber sheet in the same as being used in the check-valve A1. After the sample for measuring the contact angle was allowed to stand for 30 hours, ion-exchange water was dropped thereon. The contact angle was measured. An obtained value thereof was defined as the contact angle of the bottom surface 23 of the check-valve A1.

Check-valves B1 to B4 having the structure (a material of a sheet for the bottom surface 23 was a cycloolefin resin) shown in FIG. 1 and the shape shown in FIG. 11(3) was produced in the same manner as Example 1. While a producing process of the check-valves B1 to B4, the cycloolefin resin sheets were allowed to stand for 5 minutes, 15 hours, 30 hours and 120 hours, respectively, after an activation treatment thereof, and then ion-exchange water was injected into the check-valves B1 to B4 so as to be the reverse flow. The reverse flow minimum flow was measured. The activation treatment in the same as the producing process of the check-valves B1 to B4 was conducted to four samples for measuring the contact angle made of the cycloolefin resin sheets in the same as being used in the check-valves B1 to B4. After the samples for measuring the contact angle were allowed to stand for 5 minutes, 15 hours, 30 hours and 120 hours, respectively, ion-exchange water was dropped thereon. The contact angles were measured. Obtained value thereof was defined as the contact angle of the bottom surface 23 of the check-valves B1 to B4, respectively.

The material of the bottom surface 23 of the check-valve A1 and the check-valves B1 to B4, standing time from the activation treatment to injecting ion-exchange water, the contact angle and the reverse flow minimum flow are respectively shown in Table 6.

TABLE 6

| Check-valve No. | Material of Bottom surface | Standing time | Contact angle (degree) | Reverse flow minimum flow (mL/h) |
|---|---|---|---|---|
| A1 | Silicone rubber | 30 hours | 108.5 | <1 |
| B1 | Cycloolefin resin | 5 minutes | 53.7 | >150 |
| B2 | Cycloolefin resin | 15 hours | 68.1 | 100 |

TABLE 6-continued

| Check-valve No. | Material of Bottom surface | Standing time | Contact angle (degree) | Reverse flow minimum flow (mL/h) |
|---|---|---|---|---|
| B3 | Cycloolefin resin | 30 hours | 72.7 | 75 |
| B4 | Cycloolefin resin | 120 hours | 74.6 | 25 |

According to the check-valve which appropriately set the contact angle between the bottom surface 23 of the flow-in valve chamber 22 and ion-exchange water, the reverse flow minimum flow could be freely controlled.

INDUSTRIAL APPLICABILITY

The check-valve of the present invention can be used by being set in a microchemical chip which is used in an analysis of biological component of patients at an emergency medical practice which requires to obtain a result of the analysis rapidly; a DNA analysis for identification of DNA using a electrophoresis after extracting DNA from things left behind such as a trace amount of a bloodstain, biological fluid, hair and a biological tissue cell etc. at a crime scene, and conducting a PCR amplification for amplifying DNA; an evaluation of physical properties and drug efficacy of various drug candidates for searching a novel drug; diagnosis for custom-made medical treatment; microsynthesis of peptide, DNA or a functional low-molecular.

The microchemical chip of the present invention can be used in conducting a genetic diagnosis or healing in a medical field; various analyses in a criminal investigation field by using biological reagent; microbiological search by using an underwater apparatus in a remote location such as the ocean or lake and a reservoir etc.; and various syntheses of drug development by being set on a microreactor or analysis apparatus.

EXPLANATIONS OF LETTERS OR NUMERALS

Numerals mean as follows. 1, 1a, $1a_1$-$1a_4$, 1b, $1b_1$-$1b_4$, 1c: check-valve, 10: base sheet, 10a: water repellent sheet, 20: thin sheet, 20a: flow path sheet, 20b: valve chamber forming sheet, 21, 21a, 21b, 21c: shallow flow path, 22, 22a, 22b, 22c: flow-in valve chamber, 23, 23a: bottom surface, 24: liquid specimen pumping start part, 26: flow-out part, 30: partition film sheet, 31, 31a, 31b, 31c: through-pass hole, 32, $32a_1$, $32b_1$, 32c: inner flange, 32a: shallow flow path side inner flange, 32b: deep flow path side inner flange, 33: slit, 34, 36, 37: communicating hole 40: thick sheet, 40a: flow path sheet, 40b: valve chamber forming sheet, 40c: spacer sheet, 41, 41a, 41b, 41c: deep flow path, $41a_1$: flow path, 42, 42a, 42b, 42c: flow-out valve chamber, 43: upper surface, 44: communicating hole, 45, 45a, 45b, 45c, 45d: reaction cistern, 46: communicating hole, 50: covering sheet, 50a: water repellent sheet, 54: liquid specimen inlet, 56: outlet, 60: flow-in valve chamber forming member, 70: flow-out valve chamber forming member, 80: second partition sheet, 81c: through-pass hole, 82c: inner flange, 90: second thick sheet, 91c: second deep flow path, 92c: flow-out valve chamber, 93c: upper surface, 100: microchemical chip 100, C: central axis, $P_1$-$P_4$: primer, Q, R: flow of fluid, L, $L_1$, $L_2$: dimension of valve chamber, M, $M_1$, $M_2$: dimension of through-pass hole or slit, N, $N_1$, $N_2$: width of inner flange

What is claimed is:

1. A check-valve comprising:
   plural valve chamber forming members;
   a flow-in valve chamber and a flow-out valve chamber which are constituted by overlapping in the plural valve chamber forming members and connected to each of flow paths in which fluid flows;
   a partition sheet which is bonded to the plural valve chamber forming members while being sandwiched therebetween and has a flexible inner flange in cavities of the flow-in valve chamber and the flow-out valve chamber, in which the flexible inner flange does not close the flow-out valve chamber by flexing toward the flow-out valve chamber in a normal flow, and closes the flow-in valve chamber by flexing toward the flow-in valve chamber in a reverse flow; and
   a through-pass part which penetrates the inner flange,
   wherein the flow-in valve chamber is shallower than the flow-out valve chamber.

2. The check-valve according to claim 1, wherein the flow path penetrates at least one of the plural valve chamber forming members, and a base sheet and a covering sheet are bonded to an outermost part of the plural valve chamber forming members, respectively.

3. The check-valve according to claim 1, wherein the through-pass part is a through-pass hole which is opened at the inner flange or a slit which is cut in the inner flange.

4. The check-valve according to claim 1, wherein the fluid is liquid, and a contact angle between the liquid and an inner face of the flow-in valve chamber and a contact angle between the liquid and an inner face of the flow-out valve chamber are mutually different.

5. The check-valve according to claim 1, wherein the partition sheet is made from an elastomer having hardness from 20 to 70 in Shore-A hardness.

6. The check-valve according to claim 5, wherein the elastomer is silicone rubber, butyl rubber, ethylene-propylene rubber, ethylene-propylene-diene rubber, urethane rubber, fluoro rubber, acryl rubber, butadiene rubber, styrene-butadiene rubber, acrylonitrile-butadiene rubber, chloroprene rubber, isoprene rubber, natural rubber and/or a thermoplastic elastomer.

7. The check-valve according to claim 1, wherein the partition sheet has a thickness from 20.0 to 200 µm.

8. The check-valve according to claim 1, wherein a magnetic material is embedded and/or attached, and the inner flange is flexed corresponding to magnetic force from external side.

9. A microchemical chip comprising:
   the check-valve according to claim 1; and
   an inlet/outlet which is connected to an external side at one end of the respective flow paths.

10. The microchemical chip according to claim 9, wherein one of the inlet/outlet is a liquid specimen inlet, and another of the inlet/outlet is a liquid specimen outlet or a gas outlet.

* * * * *